(12) United States Patent
Clayton et al.

(10) Patent No.: US 7,274,767 B2
(45) Date of Patent: Sep. 25, 2007

(54) ROTATING CARRIAGE ASSEMBLY FOR USE IN SCANNING CARGO CONVEYANCES TRANSPORTED BY A CRANE

(75) Inventors: James E. Clayton, Henderson, NV (US); Paul Bjorkholm, Newport Beach, CA (US)

(73) Assignee: Varian Medical Systems Technologies, Inc., Palo Alto, CA (US)

( * ) Notice: Subject to any disclaimer, the term of this patent is extended or adjusted under 35 U.S.C. 154(b) by 0 days.

(21) Appl. No.: 11/203,491

(22) Filed: Aug. 12, 2005

(65) Prior Publication Data

US 2006/0115043 A1   Jun. 1, 2006

Related U.S. Application Data

(63) Continuation-in-part of application No. 10/356,101, filed on Jan. 31, 2003.

(51) Int. Cl.
*G01N 23/04* (2006.01)
*B63B 27/10* (2006.01)

(52) U.S. Cl. ............... 378/57; 414/140.3; 414/226.04

(58) Field of Classification Search ............ 378/22, 378/24–26, 51, 56, 57, 195, 196, 198, 208, 378/210; 414/788, 795.4, 796.9, 137.1, 139.4, 414/139.9, 140.3, 140.4, 141.3, 141.6, 226.04, 414/757, 778–783, 143.6
See application file for complete search history.

(56) References Cited

U.S. PATENT DOCUMENTS 2,659,827 A * 11/1953 Scag et al. ............... 250/493.1

| | | |
|---|---|---|
| 3,158,744 A | 11/1964 | Bernstein |
| 3,543,952 A | 12/1970 | Young |
| 3,559,822 A | 2/1971 | Lichtenford |

(Continued)

FOREIGN PATENT DOCUMENTS

WO   WO 03/053840 A1   7/2003

(Continued)

OTHER PUBLICATIONS

Shapiro, Carolyn, "Terminals Install radiation-detection equipment," The Virginian-Pilot, Dec. 21, 2002, available at http://web.archive.org/web/20030203041021/http://www.pilotonline.com/business/bz1221nit.html.

(Continued)

*Primary Examiner*—Edward J. Glick
*Assistant Examiner*—Anastasia S. Midkiff
(74) *Attorney, Agent, or Firm*—Brandon N. Sklar; Kaye Scholer LLP

(57) ABSTRACT

In one example, a radiation scanning system and method rotates a cargo conveyance after removal from a ship for proper orientation with respect to a scanning source and detector, for scanning. A movable carriage may be provided on a crane system, to rotate the cargo conveyance. A rotating flywheel on the carriage rotates in a direction opposite the direction of rotation of the cargo conveyance, to counterbalance angular momentum generated by the rotating conveyance, to avoid or minimize twisting of the carriage. Feedback is provided to control the rotation of the flywheel. Once the cargo conveyance is in the predetermined position, the conveyance is moved between the radiation source and detector for scanning by a vertically extending radiation beam.

21 Claims, 16 Drawing Sheets

U.S. PATENT DOCUMENTS

| | | | |
|---|---|---|---|
| 3,630,390 | A | 12/1971 | Tax et al. |
| 3,812,987 | A | 5/1974 | Watatani |
| 3,881,608 | A * | 5/1975 | Hupkes .................. 414/141.3 |
| 3,921,818 | A | 11/1975 | Yamagishi |
| 4,244,615 | A | 1/1981 | Brown |
| 4,400,650 | A | 8/1983 | Giebeler, Jr. |
| 4,430,568 | A | 2/1984 | Yoshida et al. |
| 4,599,740 | A | 7/1986 | Cable |
| 4,726,046 | A | 2/1988 | Nunan |
| 5,065,418 | A | 11/1991 | Bermbach et al. |
| 5,098,640 | A | 3/1992 | Gozani et al. |
| 5,111,494 | A | 5/1992 | Turner et al. |
| 5,124,658 | A | 6/1992 | Adler |
| 5,251,240 | A | 10/1993 | Grodzins |
| 5,251,768 | A * | 10/1993 | Yoshimatsu et al. ........ 212/277 |
| 5,422,926 | A | 6/1995 | Smith et al. |
| 5,495,106 | A | 2/1996 | Mastny |
| 5,524,133 | A * | 6/1996 | Neale et al. .................. 378/53 |
| 5,638,420 | A | 6/1997 | Armistead |
| 5,692,028 | A | 11/1997 | Geus et al. |
| 5,784,430 | A | 7/1998 | Sredniawski |
| 5,809,106 | A | 9/1998 | Kitade et al. |
| 5,838,759 | A | 11/1998 | Armistead |
| 5,848,115 | A | 12/1998 | Little et al. |
| 5,910,973 | A | 6/1999 | Grodzins |
| 5,917,880 | A | 6/1999 | Bjorkholm |
| 5,948,137 | A | 9/1999 | Pflaum |
| 6,009,146 | A | 12/1999 | Adler et al. |
| 6,058,158 | A | 5/2000 | Eiler |
| 6,115,128 | A | 9/2000 | Vann |
| 6,192,104 | B1 | 2/2001 | Adams et al. |
| 6,234,332 | B1 | 5/2001 | Monzen et al. |
| 6,282,262 | B1 | 8/2001 | Warburton |
| 6,292,533 | B1 | 9/2001 | Swift et al. |
| 6,301,326 | B2 | 10/2001 | Bjorkholm |
| 6,356,620 | B1 | 3/2002 | Rothschild et al. |
| 6,366,021 | B1 | 4/2002 | Meddaugh et al. |
| 6,370,222 | B1 | 4/2002 | Cornick, Jr. |
| 6,445,766 | B1 | 9/2002 | Whitham |
| 6,448,564 | B1 | 9/2002 | Johnson et al. |
| 6,453,007 | B2 | 9/2002 | Adams et al. |
| 6,459,761 | B1 | 10/2002 | Grodzins et al. |
| 6,495,837 | B2 | 12/2002 | Odom et al. |
| 6,542,580 | B1 | 4/2003 | Carver et al. |
| 6,553,094 | B1 | 4/2003 | Bernardi et al. |
| 6,580,940 | B2 | 6/2003 | Gutman |
| 6,628,745 | B1 | 9/2003 | Annis et al. |
| 6,768,421 | B1 | 7/2004 | Alioto et al. |
| 6,778,631 | B2 | 8/2004 | Franke |
| 6,778,633 | B1 | 8/2004 | Loxley et al. |
| 6,813,336 | B1 | 11/2004 | Siochi |
| 6,845,873 | B1 | 1/2005 | Chattey |
| 6,936,820 | B2 | 8/2005 | Peoples |
| 2003/0108150 | A1 * | 6/2003 | Franke ........................ 378/57 |
| 2003/0108405 | A1 * | 6/2003 | Takehara et al. ......... 414/140.3 |

FOREIGN PATENT DOCUMENTS

WO    WO 2004/085298 A1    7/2004

OTHER PUBLICATIONS

McDonald Marci, "Checkpoint Terror", U.S. News & World Report, Feb. 11, 2002, USA, available at http://www.usnews.com/usnews/biztech/articles/020211/archive_020192.htm.

Seigle, Greg, "U.S. Response I: Customs Seeks to Reverse Shipping Inspection Procedures," Jan. 18, 2002, NTI: Global Security Newswire, available at http://www.nti.org/d_newswire/issues/2002/1/18/1s.html.

Bonner, Robert C., "Speech Before the Center for Strategic and Internatinal Studies (CSIS), Washington, D.C.," Jan. 17, 2002, available at http://www.customs.ustreas.gov/xp/cgov/PrintMe.xml?xml=$/content/newsroom/commissioners_msgs/speeches_statements/archives/jan172002.ctt&location=/newsroom/commissioner/speeches_statements/archives/2002/jan172002.xml.

Aston, Adam; Cady John, "Pandora's Cargo Boxes," Business Week, Oct. 22, 2001, New York, available at http://www.businessweek.com/magazine/content/01_43/b3754050.htm.

De Moulpied, David S., Waters, David, "Cargo Screening Techniques Become More Widely Accepted," pp. 127-129, , Port Technology International, Tenth Edition, 1999.

* cited by examiner

ROTATING CARRIAGE ASSEMBLY FOR USE IN SCANNING CARGO CONVEYANCES TRANSPORTED BY A CRANE

The present application is a continuation-in-part of application Ser. No. 10/356,101, which was filed on Jan. 31, 2003, is assigned to the assignee of the present invention, and is incorporated by reference herein.

FIELD OF INVENTION

The invention relates to methods and systems for radiation scanning of objects, and more particularly, to a system and method for rotating and radiation scanning of cargo conveyances for the detection of contraband.

BACKGROUND OF INVENTION

Radiation is commonly used in the non-invasive inspection of objects such as luggage, bags, briefcases, and the like to identify hidden contraband. Contraband includes guns, knives, explosive devices, as well as illegal drugs, for example. As criminals and terrorists have become more creative in the way they conceal contraband, the need for more effective non-invasive inspection techniques has grown. While the smuggling of contraband onto planes in carry-on bags and in luggage has been a well-known, on-going concern, a less publicized but also serious threat is the smuggling of contraband across borders and by boat in large cargo containers. For example, it has been reported that only 2%-10% of the 17 million cargo containers brought to the United States by boat are inspected. ("Checkpoint Terror", U.S. News and World Report, Feb. 11, 2002, p. 52.)

One common inspection system is a line scanner, where an object to be inspected, such as luggage, is passed between a stationary source of radiation, such as X-ray radiation, and a stationary detector. The radiation is collimated into a vertical fan beam or a pencil beam and the object is moved horizontally through the beam. The radiation transmitted through the object is attenuated to varying degrees by the contents of the object. The attenuation of the radiation is a function of the density of the materials through which the radiation beam passes. The attenuated radiation is detected and radiographic images of the contents of the objects are generated for inspection. The radiographic image reveals the shape, size, and varying densities of the contents.

In a typical seaport environment, a cargo ship is docked in the seaport, and containers are lifted off from the ship by a crane. The containers may be lowered by the crane onto a truck. If it is decided to inspect the container for contraband then the truck takes the container to a designated inspection site.

Typical X-ray inspection systems, when used in a seaport or airport environment tend to be impractical due to the size of the cargo containers. Standard cargo containers are typically 20-50 feet long (6.1-15.2 meters), 8 feet high (2.4 meters) and 6-9 feet wide (1.8-2.7 meters). Air cargo containers, which are used to contain a plurality of pieces of luggage or other cargo to be stored in the body of an airplane, may range in size (length, height, width) from about 35×21×21 inches (0.89×0.53×0.53 meters) up to about 240×118×96 inches (6.1×3.0×2.4 meters). Sea cargo containers are typically about 40-50 feet long, 8 feet wide and 8 feet high (12.2-15.2×2.4×2.4 meters). Large collections of objects, such as many pieces of luggage, may also be supported on a pallet. Pallets, which may have supporting side walls, may be of comparable sizes as cargo containers.

The term "cargo conveyance" is used herein to encompass cargo containers (including sea cargo containers) and pallets.

Fixed radiation inspection systems have been proposed for inspecting large containers. For example, U.S. Pat. No. 4,430,568 to Yoshida discloses an X-ray system for the inspection of packages, including large shipping containers. A conveyor moves the package or container horizontally between the X-ray source supported on a floor and a detector array. Similarly, U.S. Pat. No. 4,599,740 to Cable discloses a fixed inspection system, where an X-ray source transmits a continuous beam of radiation across a conveyor along which the containers to be inspected are moved. The container may be moved either continuously or incrementally. The radiation transmitted through the container is detected by a "folded" sensor screen or device having two perpendicular arms, one extending vertically along a side of the container and the other extending horizontally over the top of a container during inspection. The folded sensor enables the system to have a smaller height than would otherwise be necessary in order to detect radiation transmitted through the entire container.

It has also been proposed to scan large containers with portable X-ray imaging systems. For example, U.S. Pat. No. 5,638,420 to Armistead discloses a straddle inspection system, whereby the radiation scanning system (a source and detector) is fixed to a movable frame and the frame is moved horizontally along the length of the container while the image data is sequentially recorded. Also, U.S. Pat. No. 5,692,028 to Geus et al. discloses an X-ray inspection system including a source and a detector that are mounted on a motor vehicle. The vehicle is driven past the object in order to scan the contents of the object. It has been proposed to inspect cargo conveyances with such systems.

The radiation scanning systems described above have several disadvantages. For example, the systems take up valuable space in the sea port. While the Armistead and Geus patents were designed to be portable in order to minimize the amount of space permanently dedicated to the X-ray facility, both of these systems are still large and establish a large exclusion zone when in use. In addition, all of these systems may be easily defeated within the "large container" environment. For example, once a container is unloaded from the ship and placed on the dock for delivery to the inspection station, contraband can be easily removed before inspection. The above described systems also have slow inspection speeds. The containers can be typically unloaded from a ship more rapidly than the scanner can complete its inspection.

It has also been proposed to mount a radiation detector on a crane system, to detect radiation emitted by radioactive materials within a cargo conveyance being moved by the crane system. Such systems cannot detect contraband that is not radioactive or is shielded for concealment.

U.S. Pat. No. 6,778,631 B2 purports to describe X-ray scanning systems for scanning shipping containers being moved by cranes. The X-ray sources and the detectors are not clearly shown or described. In one example, the shipping container is said to be "turned by 90° so that it can be X-rayed from the longitudinal side" for "brief" X-raying of the shipping container. It can then be determined whether further inspection is needed. (Col. 2, lines 35-40, FIG. 3). The mechanism for turning the shipping container is also not described.

SUMMARY OF THE INVENTION

Rotation of an object as large as a shipping container suspended by a crane could generate a large amount of angular momentum that could cause twisting of system components, interfering with or preventing accurate scanning.

Radiation scanning systems and methods are disclosed to enable scanning of a cargo container by orienting and aligning the cargo container in a desired position with respect to a scanning source and detector. In one embodiment of the invention, a radiation scanning system comprises a carriage capable of rotating a cargo container such that the cargo container is oriented and aligned in a predetermined position for scanning. Once the cargo container is in the predetermined position, the container is moved between the radiation source and detector for scanning along the container's longitudinal axis.

More specifically, an embodiment of a radiation scanning technique is provided for scanning an object, wherein a crane system moves the object from a first location to a second location. A radiation source and a radiation detector are proximate to the crane system and positioned such that the object may be moved between the source and the detector by the crane system. A carriage is coupled to the crane system to engage the object and to move the object from the first location to the second location. The carriage may be coupled to the object. The carriage is configured to rotate the object for scanning. A rotatable member may be coupled to the carriage. The rotatable member is rotatable in a second direction opposite to the first direction, to counterbalance angular momentum generated by the rotating cargo conveyance. This decreases or eliminates unwanted twisting of the carriage and cargo conveyance during rotation.

In another embodiment of the invention, the carriage comprises a first member coupled to the crane system and a second member coupled to the first member and capable of being coupled to the object. In this case, the second member is rotatable with respect to the first member to rotate the object, prior to moving the object between the radiation source and the radiation detector. A rotatable member is coupled to the carriage for rotation in a second direction opposite to the first direction, to counterbalance, at least in part, angular momentum generated during rotation of the first member.

In accordance with another embodiment, a method for radiation scanning an object is disclosed comprising suspending an object in the air and rotating the object to a predetermined orientation with respect to a radiation source, prior to scanning the object. The method further comprises scanning the object by a radiation source while in the predetermined orientation and detecting radiation after interacting with the object. The method may further comprise counterbalancing, at least in part, angular momentum generated by rotating the object. The angular momentum may be counterbalanced by rotating a member coupled to the object in a second direction opposite the first direction.

In accordance with another embodiment of the invention, a method of radiation scanning an object is disclosed comprising lifting an object by a crane from a ship, in a first orientation, rotating the object to a second orientation, prior to scanning the object, and counterbalancing, at least in part, angular momentum generated by rotation of the object. The method further comprises scanning the object by a radiation source in the second orientation and detecting radiation after interacting with the object.

In accordance with another embodiment, a system for radiation scanning an object is disclosed comprising means for suspending an object, means for rotating the suspended object to a predetermined orientation with respect to a radiation source, prior to scanning the object, and means for scanning the object by a radiation source. The system may further comprise means for counterbalancing, at least in part, angular momentum generated by rotation of the object.

In accordance with embodiments of the invention, the crane system may be any structure or device used to lift an object from one location and lower the object onto another location.

DETAILED DESCRIPTION OF THE PREFERRED EMBODIMENTS

Figure 1A:
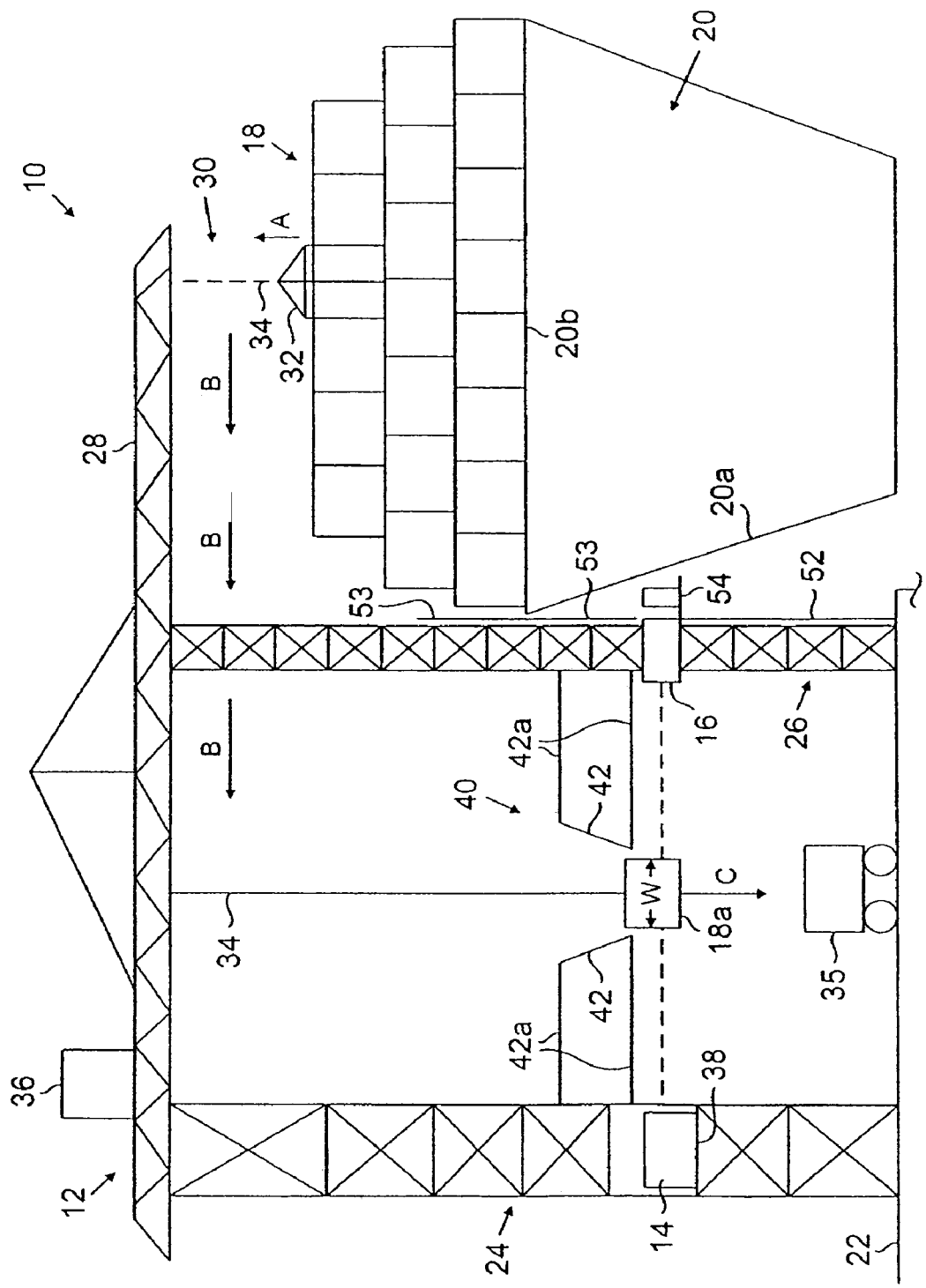
FIG. 1a is a schematic representation of a radiation scanning system supported by a crane system.

FIGS. 1a-10 show embodiments of radiation scanning systems for use at seaports, for example, disclosed in application Ser. No. 10/356,101, which was filed on Jan. 31, 2003, is assigned to the assignee of the present invention, and is incorporated by reference herein. FIG. 1a is a schematic representation of a radiation scanning system 10 comprising a crane system 12 supporting a radiation source 14 and a radiation detector 16. The crane system 12 may be a standard crane for unloading and loading cargo conveyances 18, such as sea containers and pallets, for example, from a ship 20 at a dock or seaport 22, as is known in the art. In this example, the crane system 12 may be any device used to lift an object from one location and lower the object onto another location.

The crane system 12 comprises opposing vertical structures 24, 26 supporting a boom arm 28. A conveying system 30 is supported by the boom arm 28. The conveying system 30, the details of which are not shown but are known in the art, may comprise a carriage or spreader bar 32 for securing a cargo conveyance 18 or other such object. The carriage 32 is suspended from a chain or cable 34 driven around pulleys by a motor (not shown). The conveying system 30 may lift a cargo conveyance 18 via the carriage 32 off of a ship vertically, as indicated by arrow A, move the cargo conveyance horizontally towards the seaport 22, as indicated by arrows B, and lower the cargo conveyance onto a truck 35, or onto the seaport, itself, as indicated by arrow C. The crane system 12 may be operated by an operator located in a control compartment 36, for example. The carriage 32 is released and returned by the conveying system 30 to the ship 20, to be secured to another cargo conveyance 18. The process is reversed to load cargo conveyances 18 onto the ship 20.

Figure 1B:
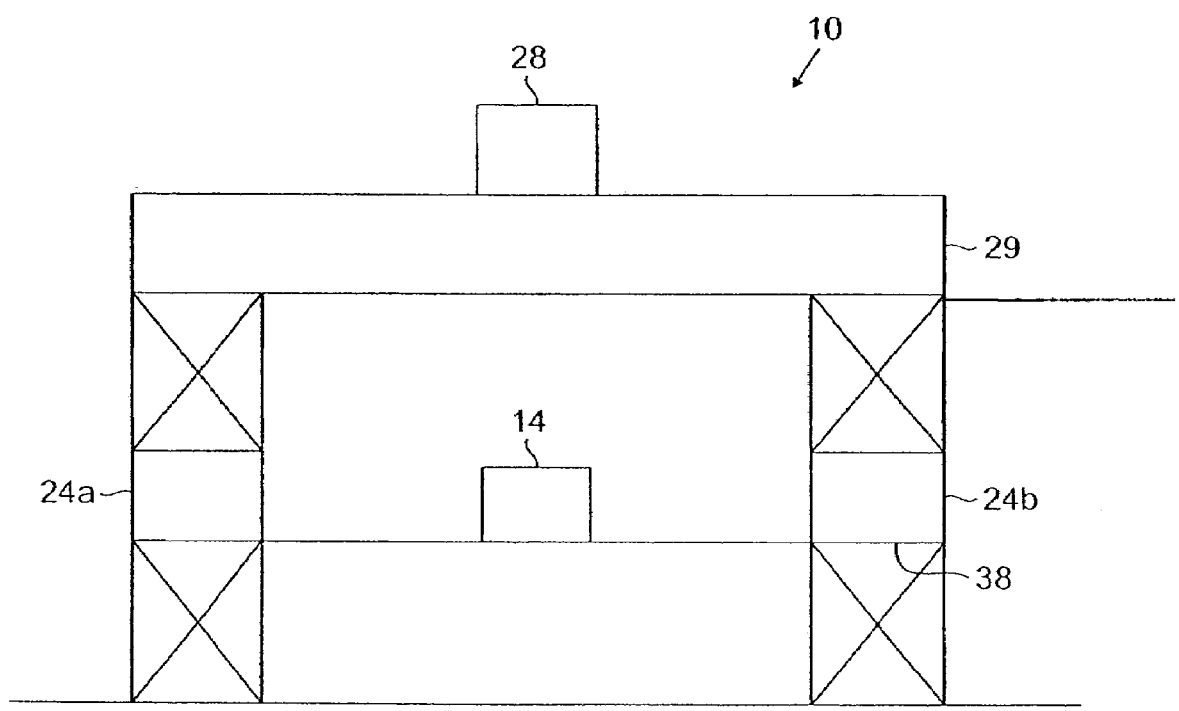
FIG. 1b is a rear view of the radiation scanning system of FIG. 1.

FIG. 1b is a rear view of the radiation scanning system 10, showing the source 14 supported on a crossbeam 38 (also shown in FIG. 1a) connecting a pair of vertical supports 24a, 24b of vertical structure 24. The detector 16, not shown in this view, is similarly supported on a cross beam between vertical supports of vertical structure 26. The guide 40 and the ship 20 are also not shown in this view. The source 14 and the detector 16 are separated by a sufficient distance for a cargo conveyance 18 or other such object to be lowered between them. Also shown in this view is an upper crossbeam 29 that supports the boom arm 28.

The radiation source 14 and detector 16 may be supported by an existing cross-beam or additional cross-beams and accompanying supporting structure may be added to support the source and/or the detector, depending on the size and structure of the crane system 12 and the desired distance between the source and the detector, for example. A standard crane system 12 may be readily retrofit to include the source 14 and the detector 16.

Figure 2:
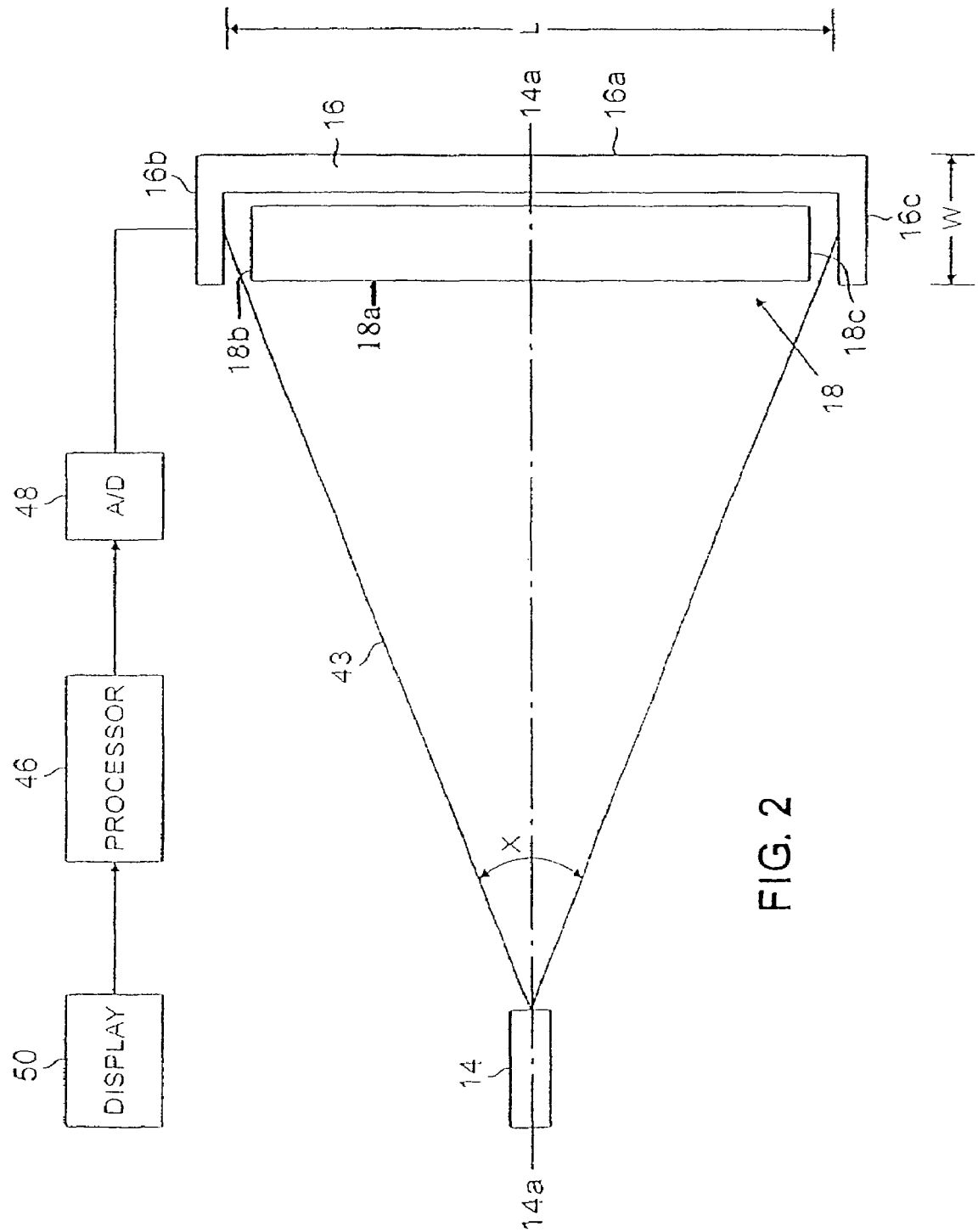
FIG. 2 is a top view of a cargo conveyance being lowered through a radiation beam emitted by a source, such as a linear accelerator, in the embodiment of FIG. 1.

While the cargo conveyance 18 is being moved between the source 14 and the detector 16 (either raised or lowered), the source emits a radiation beam 43 (as shown in FIG. 2) onto a face 18a of the cargo conveyance 18. The detector 16 detects radiation transmitted through the cargo conveyance 18. By moving the cargo conveyance 18 completely through the beam, the entire conveyance may be scanned.

Preferably, in this example, the radiation beam 43 is a horizontally diverging beam. More preferably, in this example, the radiation beam is a horizontally diverging fan beam. A cone beam may be used, as well. Here, the term "fan beam" refers to a diverging radiation-beam having essentially only one dimension, such as a horizontal direction. The term "cone beam" refers to a two dimensional diverging radiation beam, such as a radiation beam that diverges horizontally and vertically. The cone beam need not be a mathematical cone; it may be an arbitrarily shaped cone with a cross-section having an outer edge with a rectangular, square, circular or elliptical shape, for example. The radiation beam may be a rectangular asymmetric cone beam, for example. The horizontally diverging beam 43 may be defined by one or more collimators, as is known in the art. The collimator may be integrated with the source 14.

A guide 40 comprising tapered walls 42 may be provided proximate the source 14 and the detector 16 to help guide the cargo conveyance 18 as it is being moved between the source 14 and the detector 16. If the cargo conveyance 18 is scanned as it is being lowered, as in the embodiment of FIG. 1a, the guide 40 is above the level of the source 14 and detector 16. If the cargo conveyance 18 is scanned while it is being raised, the guide 40 is below the level of the source 14 and detector 16. The guide 40 may be supported by horizontal beams 42a attached to the crane's supporting structures 24, 26, for example. One pair of opposing tapered walls 42 are shown in FIG. 1a. A second pair of opposing walls, transverse to the first pair, may be provided, if desired.

FIG. 2 is a top view of a horizontally diverging radiation beam 43 scanning a cargo conveyance 18 being lowered vertically through the beam. The source 14 and detector 16 are shown. The detector 16 may be a detector array. The detector array 16 may have one long portion 16a behind the cargo conveyance 18 and two short portions 16b, 16c parallel to each other and perpendicular to the long portion 16a. The short portions 16b, 16c face the side walls 18b, 18c of the cargo conveyance 18. The short portions 16b, 16c detect radiation transmitted through the sides 18b, 18c of the cargo conveyance 18. Providing such short, parallel portions enables the detector array 16 to be more compact. Instead of the short parallel portions 18b, 18c, a longer long portion 16a may be provided to capture all the radiation transmitted through the cargo conveyance 18. The detector or detector array 16 may be curved, as well. It may be semi-circular, for example.

The radiation source 14 may be a source of X-ray radiation, such as Bremsstrahlung radiation, for example. To examine cargo conveyances having a width "W" (see FIG. 1a and FIG. 2) greater than about 5 feet (1.5 meters) by a radiation scanning system 10 in accordance with the embodiment of FIG. 1, the X-ray source 14 generates a radiation beam 43 having a peak energy greater than about 1 MeV. More preferably, the X-ray source 14 generates a radiation beam 43 having an energy greater than about 6 MeV, for example. The X-ray source 14 may be a linear accelerator, such as a Linatron™ Linear Accelerator ("Linatron™"), available from Varian Medical Systems, Inc., Palo Alto, Calif. ("Varian") for example. Other types of X-ray sources may be used as well, such as electrostatic accelerators, microtrons and betatrons, for example. X-ray tubes may also be used, particularly for cargo conveyances and other objects having a width W less than about 5 feet (1.5 meters).

To detect a fan beam, the detector array 16 may be a one dimensional detector array comprising modules of detector elements, as is known in the art. Each one dimensional detector module may comprise a single row of a plurality of detector elements. The detector elements may comprise a radiation sensitive detector, such as a scintillator, and a photosensitive detector, such as a phototube or photodiode, as is known in the art. A high density scintillator, such as a cadmium tungstate scintillator, may be used. The scintillator may have a density of 8 grams per cubic cm, for example. Appropriate cadmium tungstate scintillators are available from Saint Gobain Crystals, Solon, Ohio, U.S.A. and Spectra-Physics Hilger Crystals, Kent, U.K. for example. Detector modules having detection efficiencies of from about 10% to about 80% are preferably used, depending on the radiation spectrum of the radiation beam 43.

Multiple, closely spaced, parallel fan beams may also be defined by one or more collimators. In that case, a row of one dimensional detectors may be provided for each fan beam.

The detector array is electrically coupled to a processor 46, such as a computer, through an analog-to-digital (A/D) converter 48. The processor 46 reconstructs the data output by the detector array 16 into images which may be displayed on a monitor 50 on site or at another location. While one processor 46 and A/D converter 48 are shown, additional processors, A/D converters, and other signal processing circuits may be provided, as is known in the art.

If a cone beam is used, the detector array may comprise one or more rows of two dimensional detector modules. A two dimensional detectors module may comprise a plurality of rows and columns of detector elements.

The horizontal length of a horizontally diverging beam 43 at the face 18a of the cargo conveyance 18 may be slightly greater than the width of the conveyance. The vertical height of a fan beam at the face 18a may be from about 2 mm to about 10 mm, for example. If a cone beam is used, it may have a vertical height of from about 200 mm to about 400 mm at the face 18a, for example.

Collimators,(not shown) may also be provided between the object and the detector array 16 to block scattered radiation from reaching the detector array 16.

Shielding may be provided as needed. Lead curtain shields 52, 53 may be provided behind the detector 16 to capture scattered radiation. Curtain 53 prevents scattered radiation from crossing the deck 20b of the ship 20, where there may be workers. A radiation stop 54 may be provided behind the detector 16, supported by the crane system 12. The operator compartment 36 may be shielded to protect the operator. Shielding, such as additional lead curtains, may also be provided on the sides of the crane system 12 as well, if desired. The hull 20a of the ship 20 may provide shielding instead of or in addition to the radiation stop 54 and/or at least part of the lengths of the lead curtains 52, 53. An advantage of this embodiment of the invention is that radiation is used in regions that are normally unoccupied, decreasing shielding requirements as compared to at least certain prior art systems.

The radiation scanning system 10 will generally be able to examine cargo conveyances 18 as fast as they can be moved by the crane system 12. For example, if the radiation source is a linear accelerator generating a fan beam having a width of about 5-7 mm at the face 18a of the cargo container 18 and emitting radiation beams at a rate of 300 pulses per second, it would take about 2 seconds to scan a cargo conveyance 18 having a height of about 2.5 meters, with a spatial resolution of about 5 mm.

A radiation beam 43 emitted along a longitudinal axis 14a (shown in FIG. 2) of a typical radiation source 14 has its highest intensity along the axis. The intensity drops rapidly as the angle from this axis 14a increases. It is therefore preferable not to emit a radiation beam of too wide of an angle. For example, it is preferred that the angle of the beam not exceed 30 degrees. In order to illuminate the entire face 18a of a long object, such as a sea container, with a narrow beam, however, the source 14 must be far from the face. Intensity also drops by the square of the distance between the source 14 and the face 18a. In the example of FIG. 2, if the cargo conveyance is a sea container having a length L of 40 feet (12.2 meters) long, a radiation beam 43 emitted over an angle X of about 25 degrees must be about 43 feet (13.1 meters) from the face 18a to illuminate the entire face. The angle X of the radiation beam 43 and the distance between the source and the face 18a are factors to be balanced in the design of the radiation scanning system 10.

Figure 3:
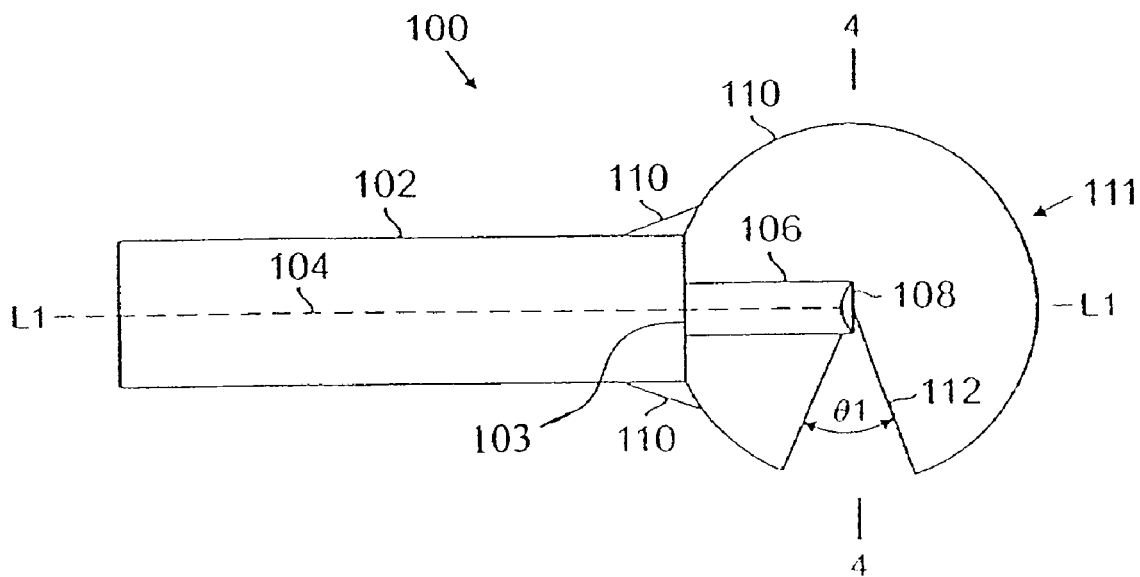
FIG. 3 is a side view of an alternative source for use in the embodiment of FIG. 1.

FIG. 3 shows an alternative configuration for the radiation source 14 that enables the source to be much closer to the cargo conveyance 18, and still illuminate the entire face 18a of a cargo conveyance with a more uniform radiation beam than a beam emitted by the source 14 of FIG. 2. The X-ray source 100 in FIG. 3, referred to as a "panoramic" radiation source, is described in application Ser. No. 10/199,781 filed on Jul. 19, 2002, assigned to the assignee of the present invention and incorporated by reference herein. The panoramic source 100 comprises a linear accelerator body 102, which may be a Varian Linatron™, as described above, or may have other configurations known in the art. The linear accelerator body 102 has an open output end 103. An electron beam 104, shown in phantom, is accelerated as it follows a path through the linear accelerator body 102 along a longitudinal axis L1 of the body. The electron beam 104 exits the accelerator body from the output end 103. A proximal end of a tube 106, referred to as a drift tube, is coupled to the output end 103 of the linear accelerator body 102, in communication with and extending from the open output end. The drift tube 106 may have a diameter of from about 6 to about 10 mm, for example. The drift tube 106 may be the same material as the linear accelerator 102, to facilitate the connection of the drift tube to the linear accelerator body. The drift tube 106 and linear accelerator body 102 may be metal for example. The drift tube and linear accelerator body may be other materials, as well.

A target material 108 of a metal with a high atomic number and a high melting point, such as tungsten or another refractory metal, is provided at the distal end of the drift tube 106. Shielding material 110, such as tungsten, steel or lead, is provided around the drift tube 106, and the target material 108 and may extend over a distal portion of the linear accelerator body 102, as well. The shielding material 110 may be in the shape of a sphere, for example, and the target material 108 may be at the center of sphere, within the drift tube 106. The shielding material 110 may also have other shapes. The drift tube 106, the target material 108 and the shielding material are referred to as a "shielded target 111".

Figure 4:
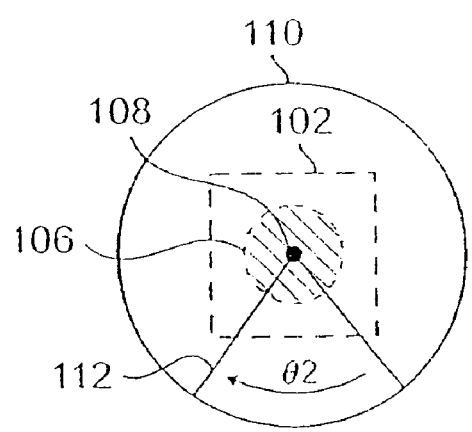
FIG. 4 is a front view of the source of FIG. 3.

A collimating slot 112 extends from the end of the drift tube 106, through the shielding material 110, transverse to the longitudinal axis L1 of the linear accelerator body 102. The slot 112 is shaped to collimate the X-ray beam emitted by the target material into a desired shape, such as into a fan beam or a cone beam, which is emitted from the shielded target in a direction perpendicular to the axis L1 of the accelerator body 102. The slot 112 has a first angular dimension $\theta 1$. FIG. 4 is a cross-sectional view of the shielded target 111 through line 44 of FIG. 3, showing a second angular dimension $\theta 2$ of the slot. The first angular dimension $\theta 1$ and the a second angular dimension $\theta 2$ define the shape of the radiation beam 43. In a preferred use, the source 100 is oriented so that the first angular dimension $\theta 1$ defines the vertical height of the radiation beam 43 and the second angular dimension $\theta 2$ defines the horizontal angle of the beam, as shown in FIG. 5, discussed below.

The electron beam 104 emitted by the linear accelerator body 102 along the longitudinal axis L1 passes through the drift tube 106 and impacts the material 108. Bremsstrahlung X-ray radiation is emitted from the target material 108 in all directions. The radiation emitted in the direction of the collimating slot 112 is collimated into the desired shape and emitted from the device 100. The shielding material 110 absorbs radiation emitted in other directions. While the intensity of the radiation emitted perpendicular to the direction of the electron beam impacting the target material may be much less than the intensity of the radiation emitted in the forward direction, by defining the horizontal angle and the beam by the second angular dimension θ2, the radiation emitted across the entire radiation beam 43 has substantially the same intensity. Since the second angular dimension θ2 may be any desired angle up to 180 degrees, the source 100 may be very close to the face 18a of the cargo conveyance 18. The intensity drop due to distance is therefore much less than in other configurations.

Figure 5:
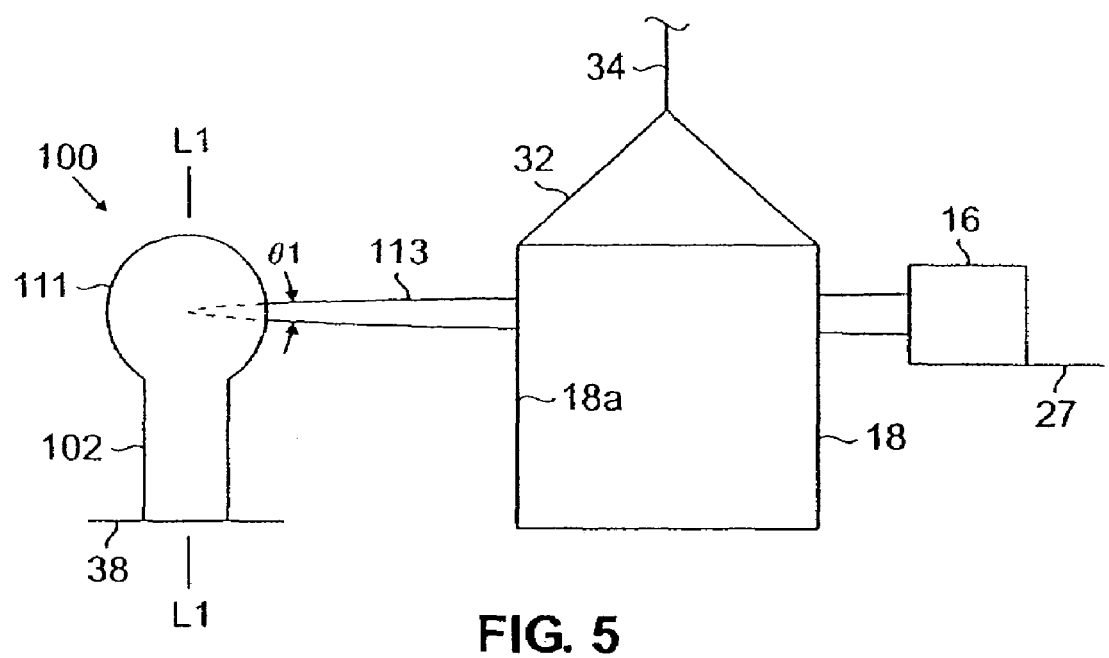
FIG. 5 is side view of the source of FIG. 3, in use in the radiation scanning system of FIG. 1.

FIG. 5 shows the radiation source 100 with a shielded target 111 supported by the crane cross-beam 38, the detector 16 supported by a crane cross-beam 27 and a cargo conveyance 18 supported by a carriage 32 suspended from a cable 34. The remainder of the crane system 12 is not shown. The cargo conveyance 18 is being moved between the source 100 and the detector 16. The radiation source 100 is oriented with the longitudinal axis L1 of the accelerator body 102 being vertical. To define a vertical height of a fan beam, the first angular dimension θ1 of the slot 112 may range from less than 1 degree to about 5 degrees. To define a vertical height of a cone beam, the first angular dimension θ1 beam may range from about 5 degrees to about 45 degrees, for example. The second angular dimension θ2 may be any desired angle such as may be any angle required to illuminate the entire width of the face 18a of the cargo conveyance 18. The angle may be 30 degrees or more, for example.

Figure 6:
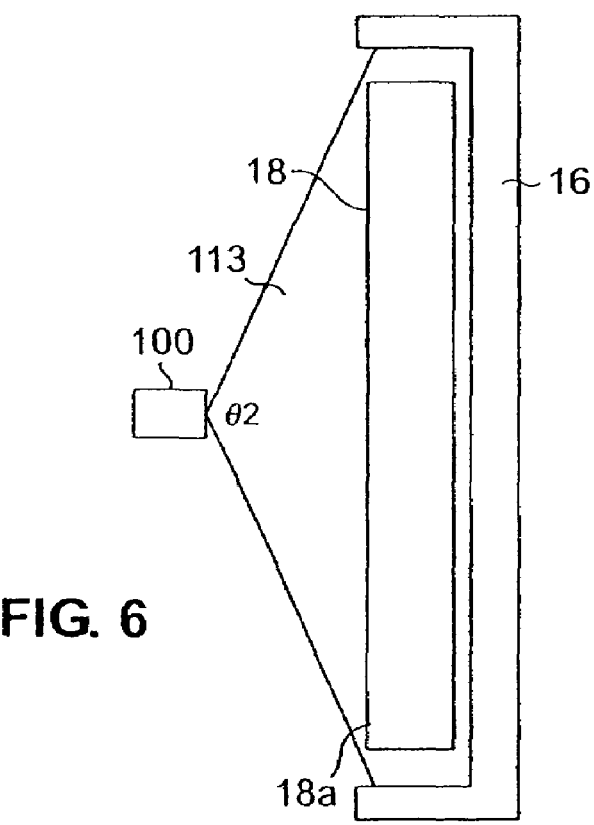
FIG. 6 is a top view of a cargo conveyance being lowered through a radiation beam emitted by the source of FIG. 3.

FIG. 6 is a top view of a cargo conveyance 18 being moved through, a radiation beam 113 emitted by a panoramic radiation source 100. In this example, the second angular dimension θ2 is about 135 degrees. The source 100 may be about 8.5 feet (2.6 meters) from the face 18a of the cargo conveyance 18. Since the axis L1 of the accelerator body 102 is parallel to the face 18a of the cargo conveyance 18, the source 100 may be easier to support on a cross beam of the crane system 12.

Figure 7:
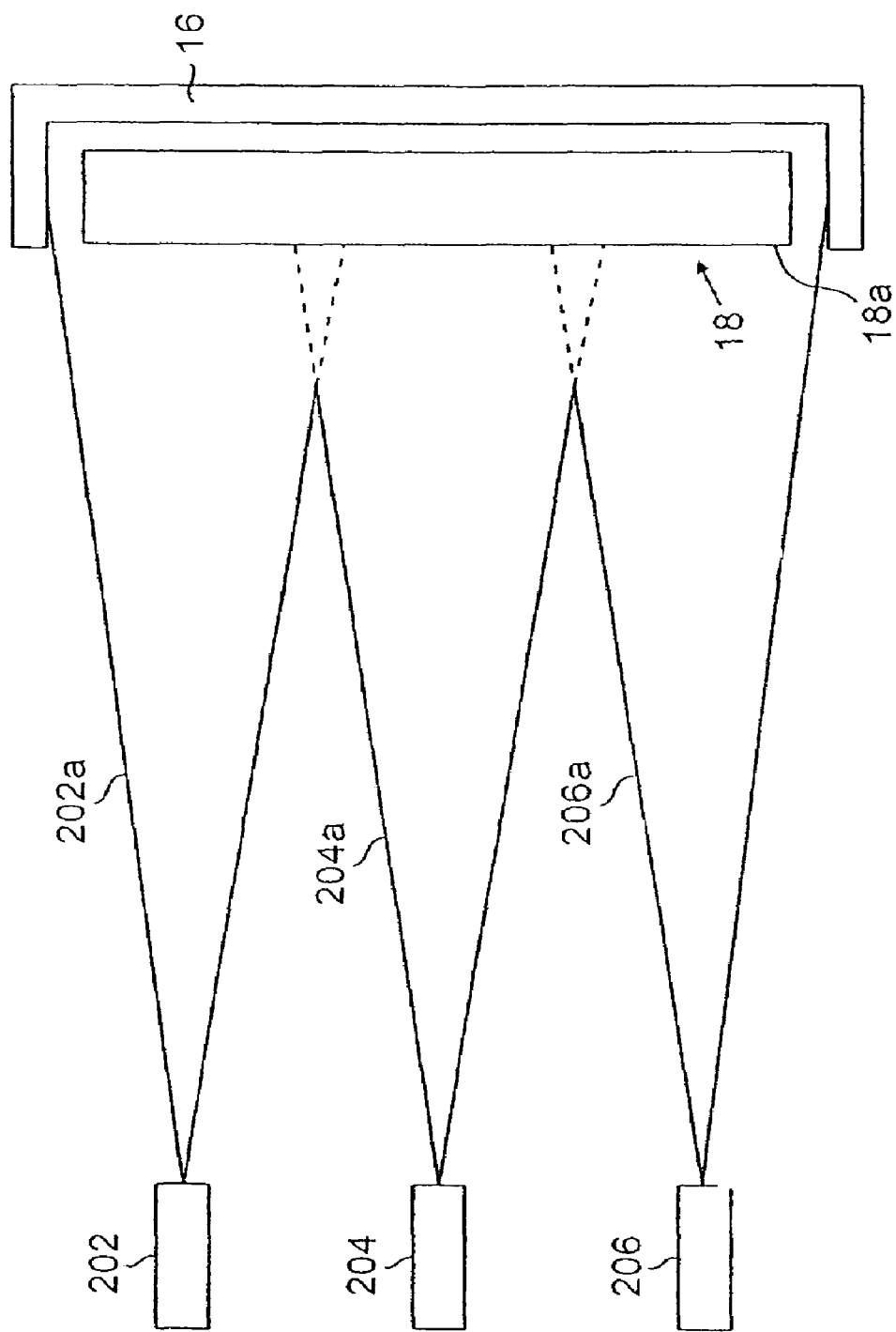
FIG. 7 is a partial top view of a cargo conveyance being lowered through three radiation beams emitted by three respective sources, in the embodiment of FIG. 1.

Instead of trying to cover the full length of the face 18a of the cargo conveyance 18 with a single, horizontally diverging radiation beam, as shown in FIGS. 2 and 6, multiple radiation beams may be provided to scan the entire face, with each beam scanning a portion of the face. In FIG. 7, multiple radiation sources 202, 204, 206 are provided, each emitting a respective radiation beam 202a, 204a, 206a illuminating a portion of the face 18a of the cargo conveyance 18. Each beam 202a, 204a, 206a preferably illuminates slightly more than one-third of the face 18a. In this instance, it is preferred that each beam slightly overlap an adjacent beam, to ensure complete coverage of the face 18a. Each source emits a horizontally diverging radiation beam over an angle of about 10 degrees to about 30 degrees, for example. Each source 202, 204, 206 may be a linear accelerator, for example, such as the Varian Linatron™ discussed above. The sources may illuminate the face simultaneously, or alternately. Alternating scanning by each source 202, 204, 206 is preferred. Each source 202, 204, 206 may alternately be on for one or a plurality of pulses within a data acquisition window of about 1 ms, for example. While three sources 202, 204, 206 emitting three beams 202a, 204a, 206a are shown, more or fewer sources and beams may be provided.

Since the angle each radiation beam 202a, 204a, 206a is emitted over is less than would be required if a single source 14, such as a single linear accelerator (see FIG. 2), was used, the entire cargo conveyance face 18 is exposed to a more uniform higher intensity radiation. In addition, the sources 202, 204, 206 may be closer to the face 18a, decreasing the intensity loss due to distance.

Figure 8:
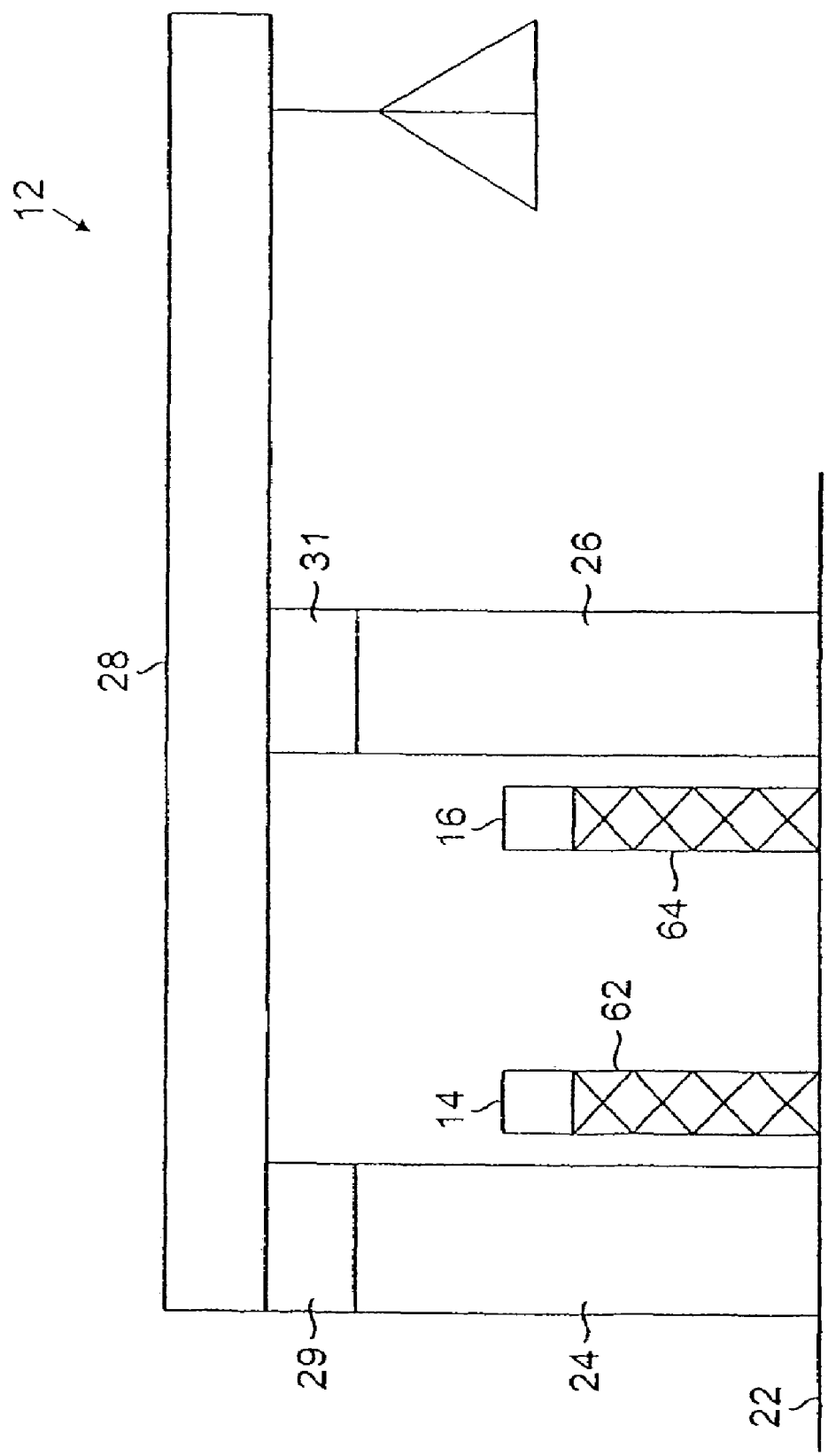
FIG. 8 is a side view of another radiation scanning system supported by a crane system, wherein a radiation source and a detector are supported by the ground proximate the crane system.
Figure 9:
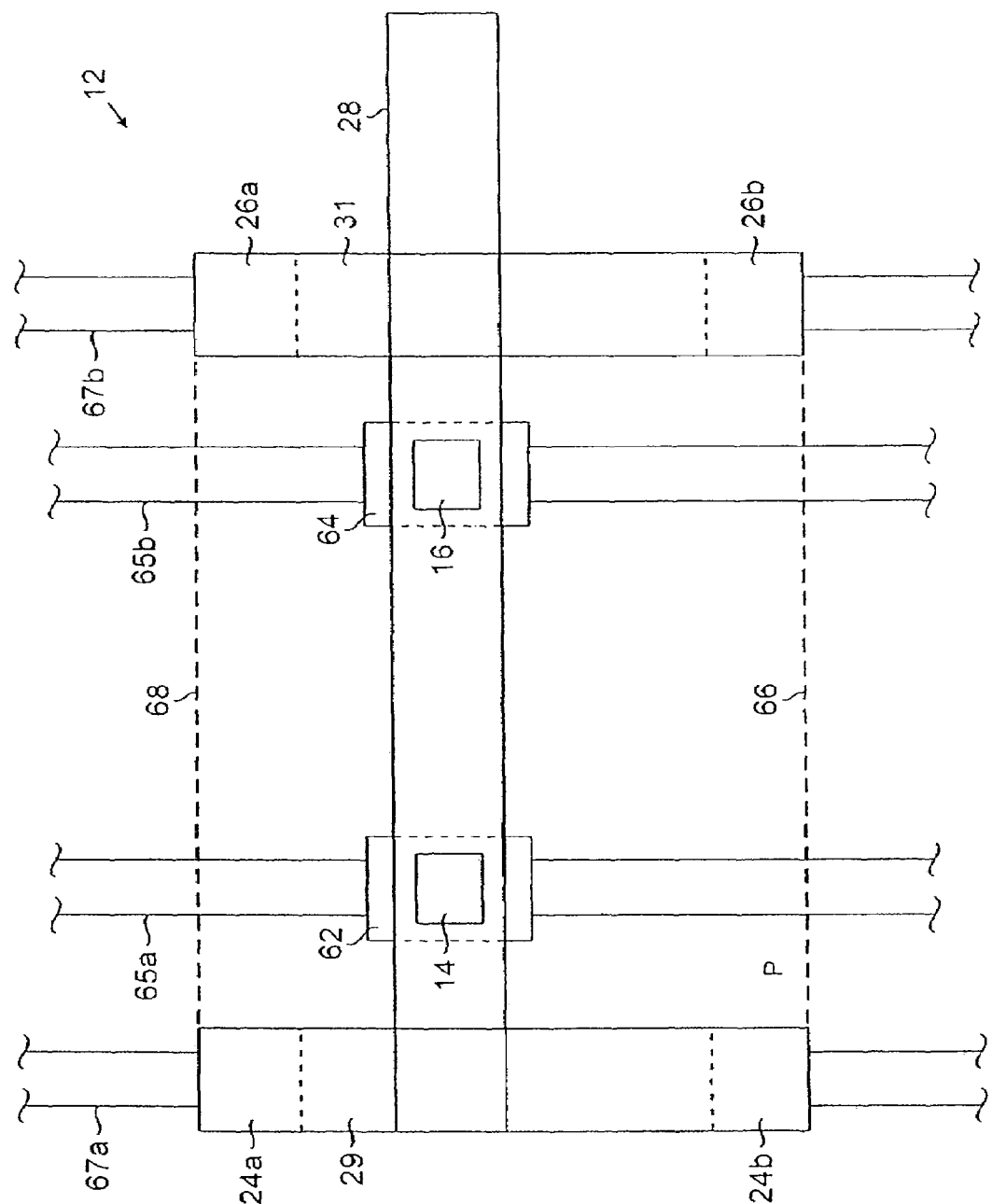
FIG. 9 is a top view of the embodiment of FIG. 8.

Instead of supporting the radiation source 14 and/or the detector 16 on the crane system 12, the source and the detector may be supported by the seaport 22, as shown in FIG. 8. The source 14 and/or detector 16 may be mounted on one or more supports 62, 64, respectively. The supports 62, 64 may be mobile. They may be movable along rails 65a, 65b on the seaport 22, for example, as shown in the top view of FIG. 9. The crane system 12 may be movable along rails 67a, 67b on the seaport 22, as well. Supporting the source 14 and/or the detector 16 by mobile supports 62, 64, facilitates the setup and precise positioning of the source 14 and the detector 16, regardless of the size of the crane system 12. FIG. 9 also shows the source 14 and detector 16 in a preferred position within a profile P of the crane system 12, defined by dotted lines 66, 68 and the vertical structures 24a, 24b, 26a, 26b, so that additional space is not taken up by the source and detector. However, the source 14 and detector 16 may be in any location through which the crane system 12 can move a cargo conveyance 18. For example, if the boom arm 28 is pivotable about a vertical axis, the cargo conveyance 18 may be moved through a location outside of the profile P of the crane system 12.

Figure 10:
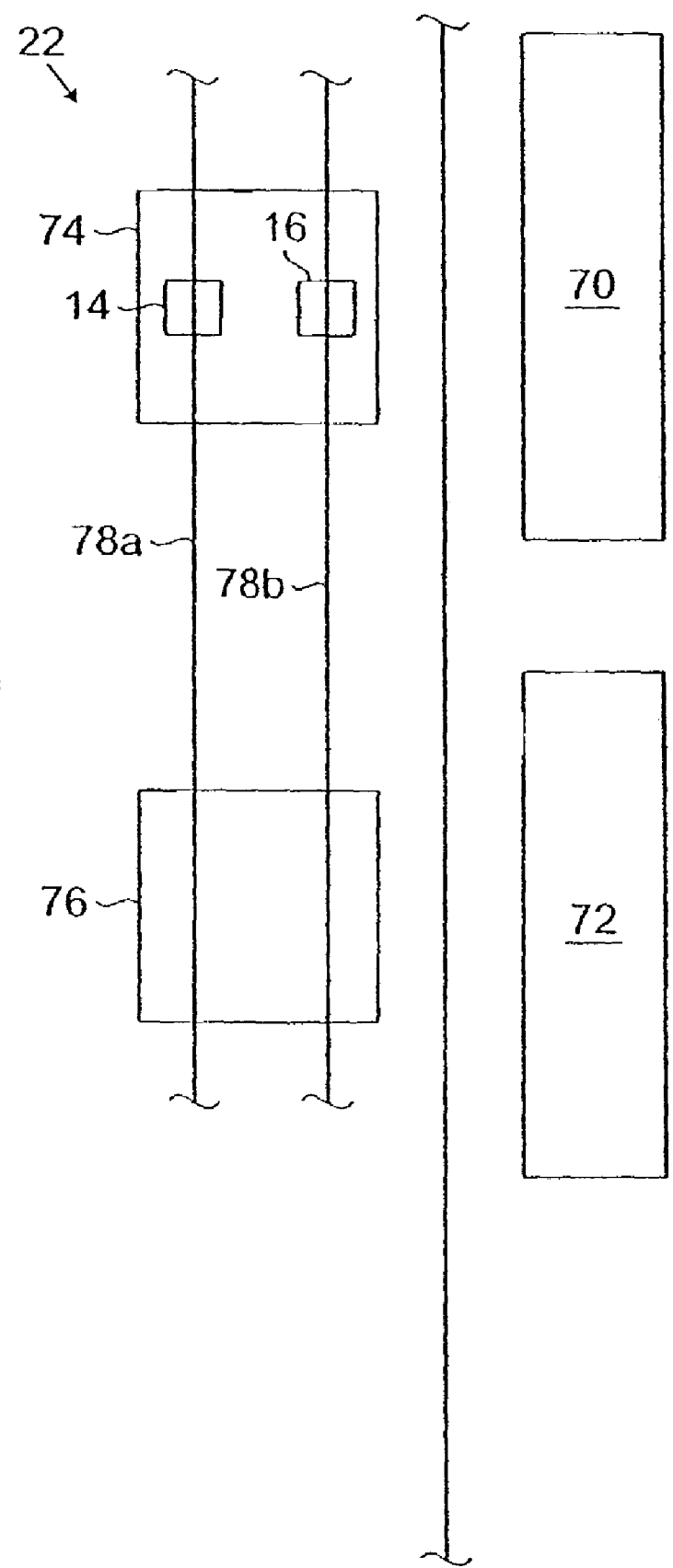
FIG. 10 is a top view of a seaport, incorporating the radiation scanning system of FIG. 8.

This configuration enables a more efficient use of a radiation scanning system in a seaport. FIG. 10 is a top view of the seaport 22. Two ships 70, 72 are shown docked at respective docking stations of the seaport 22. Two crane systems 74, 76 are positioned at the docking stations, to unload or load cargo conveyances (not shown in this view) off of or onto the ships 70, 72, respectively. More docking stations may be provided, with a crane dedicated to each station. The source 14 and the detector 16 are shown movably supported on rails 78a, 78b, at the first docking station, to scan cargo conveyances being unloaded from or being loaded onto the ship 70. After completion of the unloading and loading of the ship 70, the source 14 and the detector 16 may be moved to the second docking station, to scan cargo conveyances being unloaded from or loaded onto the ship 72. Scanning may be coordinated among two or more stations so that the source 14 and detector 16 are at one station to scan cargo conveyances being unloaded from or loaded onto a ship, another ship is docking or preparing to be unloaded or loaded at the other station. One or a few radiation scanning systems may thereby be efficiently used to examine cargo conveyances being unloaded or loaded from or to multiple ships at the seaport, at lower cost, than mounting a radiation scanning system on each crane system. To move the source 14 and the detector 16, a conveying system may be provided along the rails 78a, 78b, for example.

Figure 11:
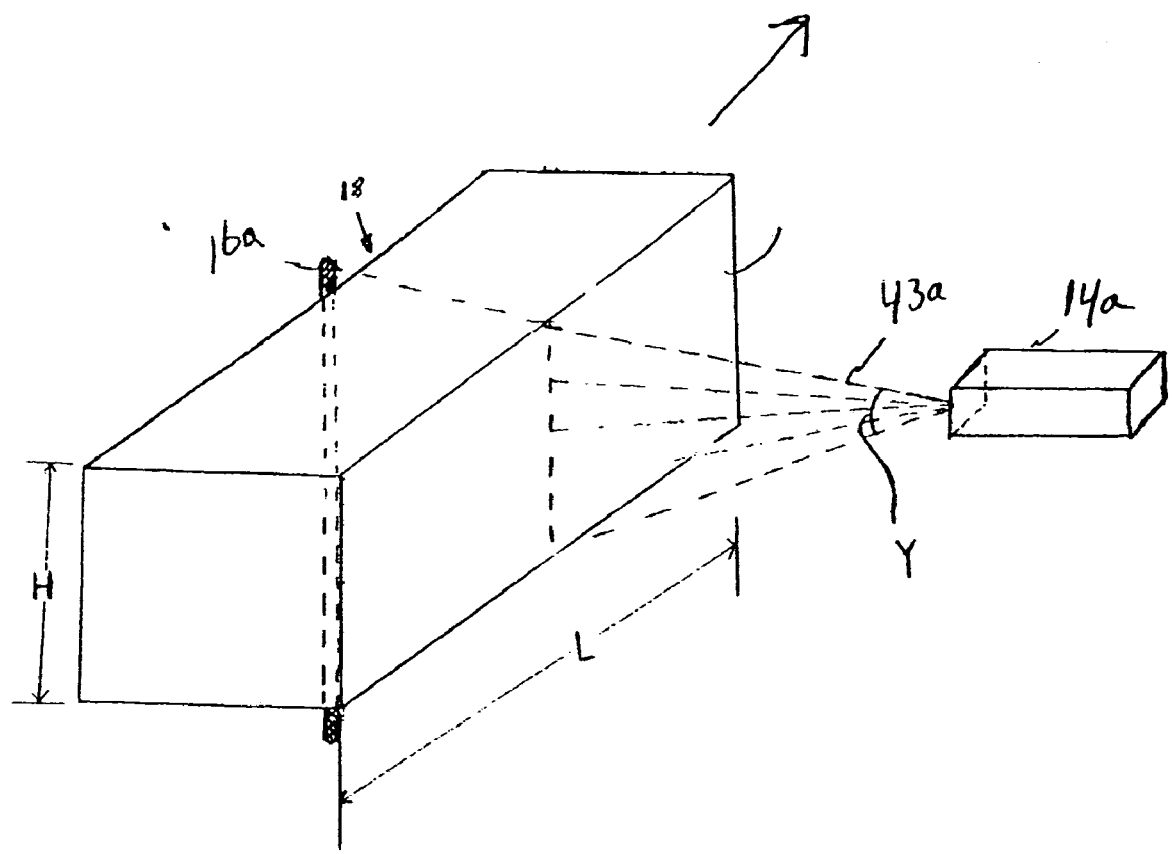
FIG. 11 is a perspective view of a cargo container being passed through a radiation beam emitted by a radiation source, in accordance with an embodiment of the invention.

While in the embodiments above, the cargo conveyance 18 is scanned by one or more horizontally extending radiation beams while the conveyance is lowered or raised, in accordance with another embodiment, the conveyance is scanned by a vertically extending radiation beam while being moved horizontally (along arrow B in FIG. 1a, for example) by the conveying system 30. In that case, the radiation source 14 and the detector 16 may be supported by the crane system 12 or by supports 62, 64, so that they are aligned along an axis perpendicular to the horizontal direction of motion of the cargo conveyance 18 during loading onto or unloading from a ship 20. A vertically diverging radiation beam 43a may then be used to scan the object, as shown in FIG. 11. The vertically extending radiation beam 43a is detected by a vertically extending detector 16a. By scanning the vertical height H of the cargo conveyance 18 as the cargo conveyance 18 moves horizontally, the angle Y over which the beam propagates may be less than the angle X of the beam 43 in FIG. 2. The intensity of the beam may therefore be more uniform than if the beam is more widely dispersed, such as if a horizontal beam is used, as described above.

Figure 12:
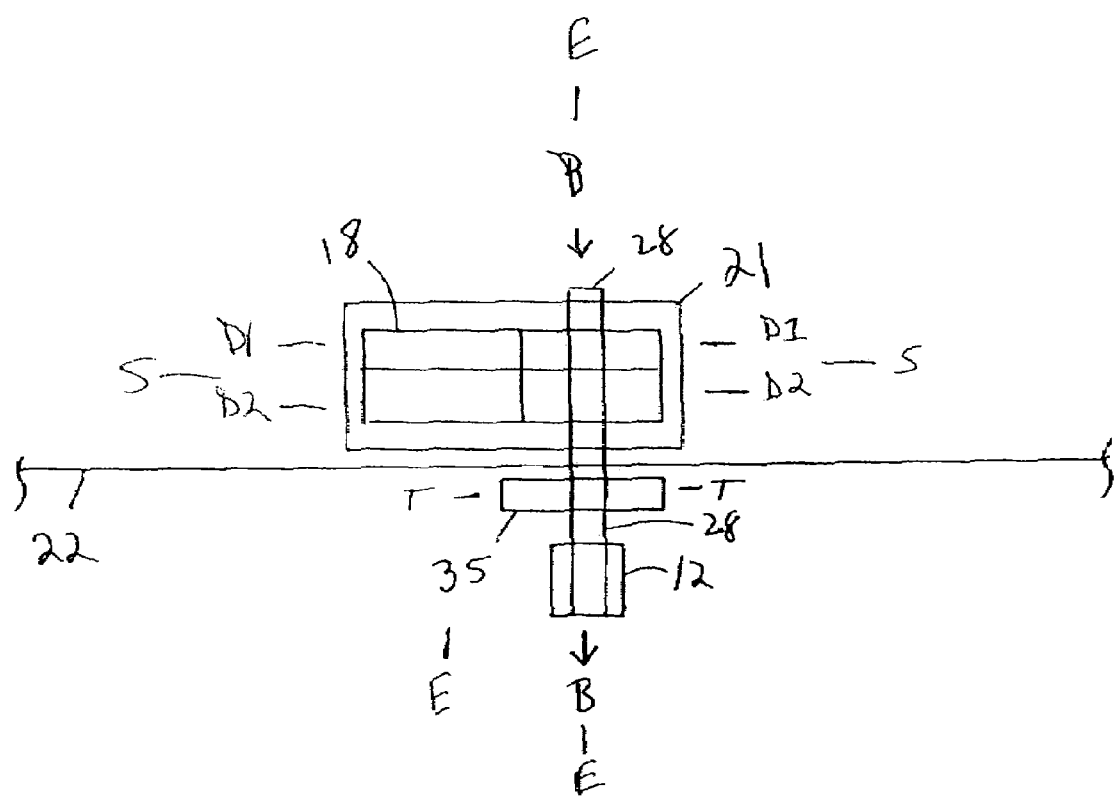
FIG. 12 is a top schematic representation of an example of a cargo ship at a dock.

The orientation of the cargo conveyance 18 on a ship may be such that, as the conveyance 18 is unloaded from the ship 20 by the crane 28, vertical scanning is difficult. FIG. 12 is a top schematic representation of an example of a cargo ship 21 at the dock 22. The crane system 12 of FIG. 1 is also shown. The cargo conveyances 18 are stacked in two rows on the ship 21 so that the long axes "D1, D2" of two respective rows of the conveyances are parallel to the long axis "S" of the ship. Short axes E1, E2 of the cargo conveyances 18, which are aligned with the direction of movement B and the boom arm 28 of the crane system when the arm is positioned to remove that cargo conveyance, are shown as well. As noted above, shipping containers are typically 20-50 feet long, 8 feet wide and 8 feet high (12.2-15.2×2.4×2.4 meters). A top level of only four cargo conveyances 18 and only two rows of cargo conveyances 18 are shown in FIG. 12, for ease of illustration. It is understood that many more cargo conveyances 18 are typically stacked in many levels and many rows, as shown on the ship 20 in FIG. 1, for example.

During unloading from the ship 21 by the crane system 12, the cargo conveyance 18 may be moved in a direction perpendicular to the long axis 5, along the direction of the arrow B in FIG. 12, for placement on the truck 35. The truck 35 also has a long axis "T" parallel to the axes D1, D2 of the cargo conveyances 18 and parallel to the axis S of the ship. The axis T is also perpendicular to the direction of movement B. The truck 35 may approach and leave a cargo conveyance loading/unloading position on the dock or seaport 22, along the direction of the axis T. Because the long axes D1, D2 are perpendicular to the direction of movement B, the orientation of the axis C is not conducive to scanning by a vertically extending radiation beam. In order to scan such a cargo conveyance 18 as it is being removed from (or loaded onto) the ship 21 or the truck 35, in accordance with an embodiment of the invention, the conveyance is rotated into a predetermined orientation for radiation scanning. After scanning, the cargo conveyance 18 may be rotated again into another predetermined orientation for loading onto a truck or onto the seaport 22.

In accordance with an embodiment of the invention, an assembly may be provided to rotate the cargo conveyance 18 from a first position with a long axis D1, for example, perpendicular to the direction of movement B of the conveyance 18, to a second position where the axis D1 is aligned with or is along the direction of movement B of the crane—prior to scanning the contents of the cargo conveyance. The conveyance 18 may be rotated about 90 degrees, for example. In addition, depending upon the desired orientation of the cargo conveyance 18 at the time of loading, the conveyance may be rotated again for proper placement onto the truck 35 or other unloading destination. If the cargo conveyance 18 is to be scanned prior to being loaded onto the ship 21, it may be rotated after removal from the truck 35, as well.

Figure 13:
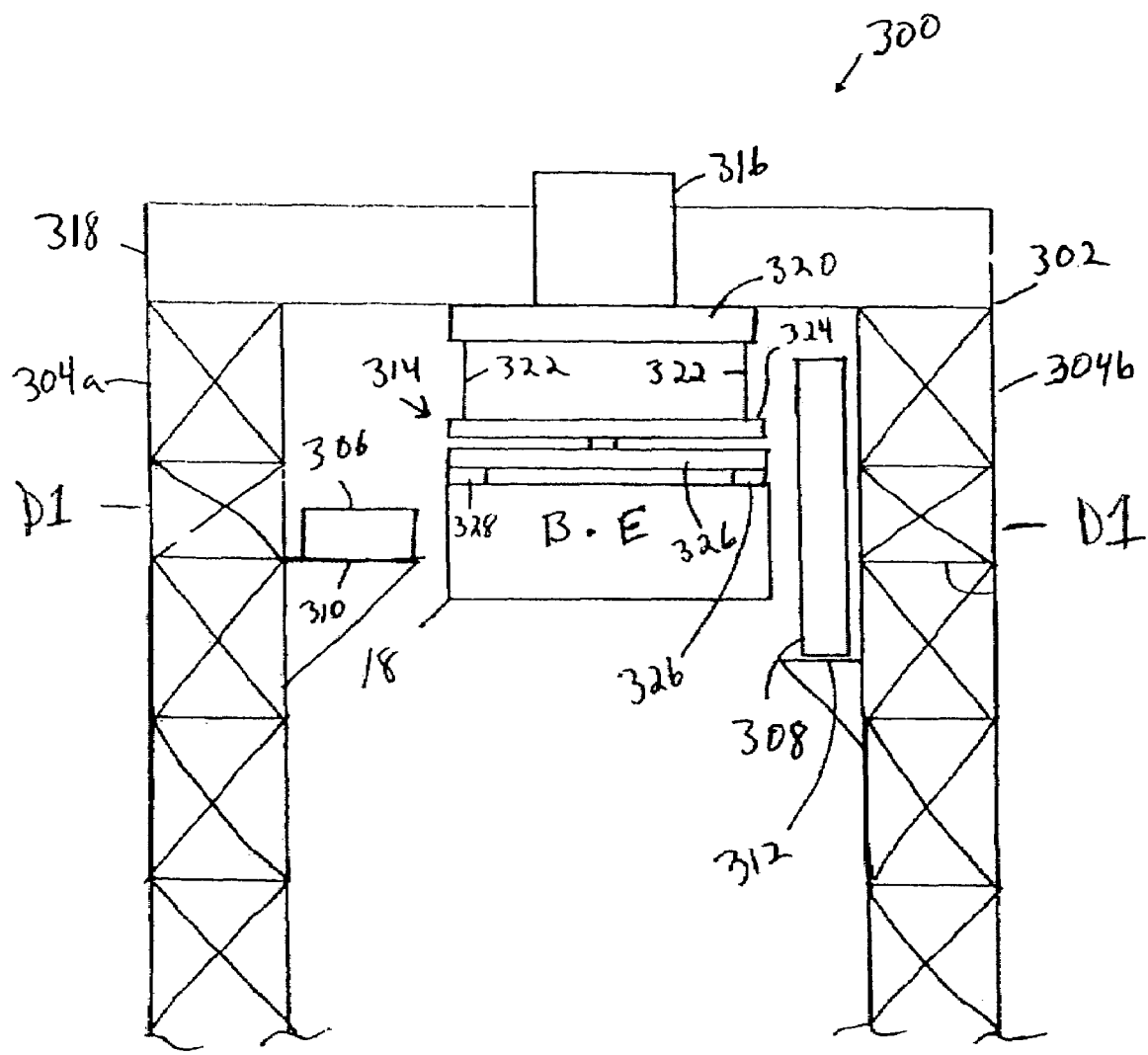
FIG. 13 is an example of a radiation scanning system in accordance with an embodiment of the invention, mounted to a crane system similar to the crane system of FIG. 1.

FIG. 13 shows an example of a radiation scanning system 300 in accordance with an embodiment of the invention, comprising a crane system 302 similar to the crane system 12 of FIG. 1. The upper portion of a front vertical structure 304, which corresponds to the vertical structure 26 in the crane system 12 of FIG. 1, is shown. A radiation source 306 and a radiation detector 308 are supported by the vertical structures 304a, 304b, respectively.

The lower portion of the crane system 300, the ship 21, and the seaport 22 are not shown in this view for ease of illustration. It is understood that the crane system 300 in this example is being portrayed schematically and that the crane system 300 may be any of a number of standard cranes currently in use for unloading and loading cargo conveyances, such as sea cargo containers and/or pallets, for example, from a ship 21 at a seaport 22, as is known in the art. In accordance with embodiments of the invention, the crane system 302 may be any structure or device used to lift an object from one location and lower the object onto another location.

The radiation source 306 and/or the detector 308 may be supported by platforms 310, 312, respectively, connected to the vertical structures 304a, 304b, respectively. They may also be supported directly by the vertical structures 304a, 304b, (as shown in FIG. 1a) or in other ways. In FIG. 13, the cargo conveyance 18 is being moved, toward the source 306 and the detector 308 along the direction of movement B, and out of the page.

FIG. 13 also shows a carriage assembly 314 supporting a cargo conveyance 18 oriented with its long axis D1 perpendicular to the direction of movement B and it's short axis E aligned with the direction of movement, as the conveyance would be positioned after being raised from or about to be lowered onto the ship 21. This orientation is not suitable for scanning with a vertically extending beam emitted from the source 306, as discussed above. The carriage assembly 314 is suspended from a boom arm 316. A crossbeam 318 supports the boom arm 316. In this example, an operator's compartment 320 is supported on the boom 316, and cables 322 suspended from the operator's compartment may support the carriage assembly 314. In other configurations, such as in FIG. 1a, the operator compartment 36 is in a different location. In that case, the carriage assembly 314 may be suspended from another structure coupled to the boom arm 28.

In one example of an embodiment of the invention, the carriage assembly 314 comprises an upper member, such as an upper spreader bar 324, rotatably coupled to a lower member, such as a lower spreader bar 326. The spreader bars 324, 326 may be rotatably coupled through a kingpin (not shown), and bearing 340 (shown in FIG. 16), for example. The lower spreader bar 326 engages and supports the cargo conveyance 18 by couplers 328, or other techniques known in the art. Four couplers may be located at the bottom surface of lower spreader 326b one at each corner of the lower spreader bar's bottom surface, for example. The cables 322 may comprise metal chains, metal ropes, or the like, as is known in the art.

Figure 14:
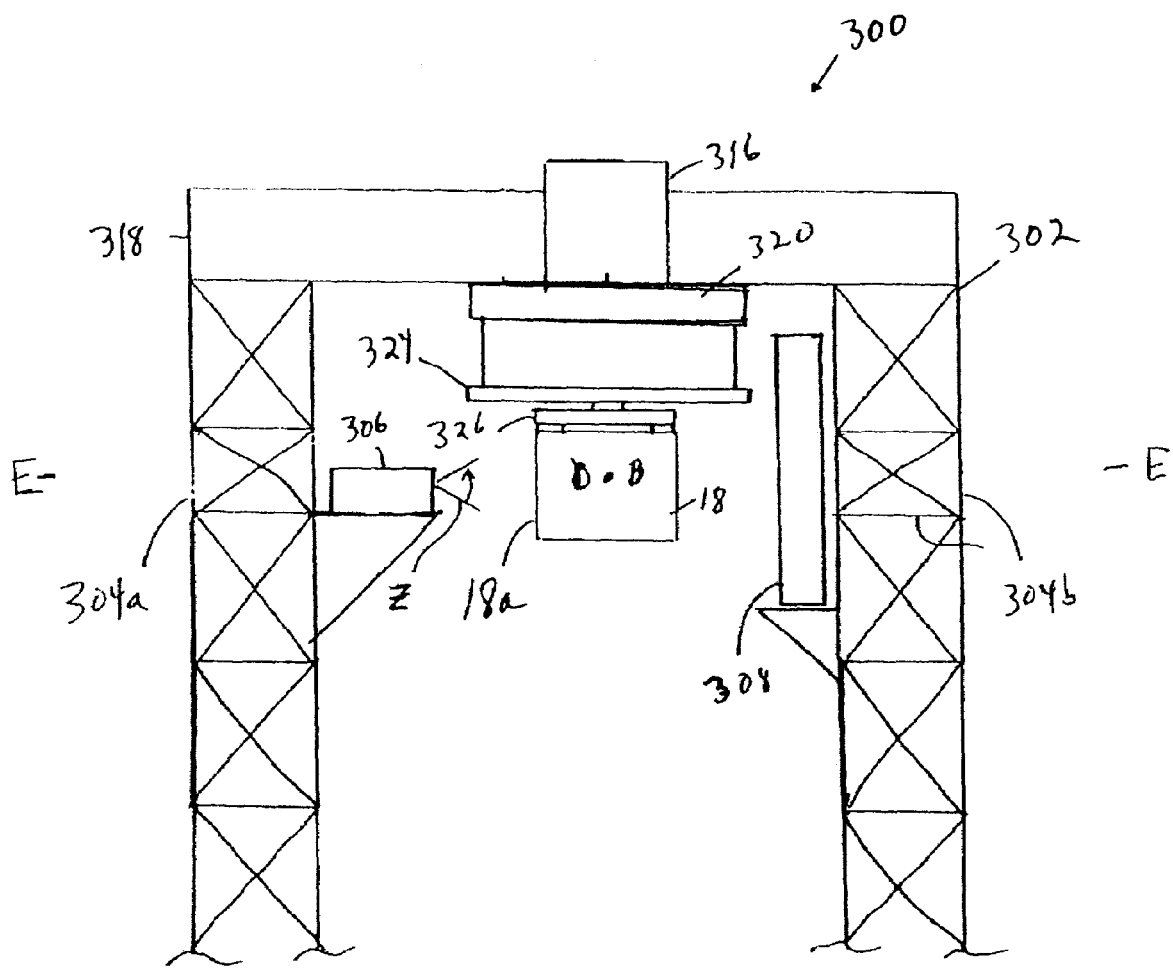
FIG. 14 is a front view of an upper portion of the scanning system of FIG. 13, with a cargo conveyance rotated 90 degrees with respect to its original orientation for scanning, with its long axis D1 aligned with the direction of movement B (both out of the page in this view)

The lower spreader bar 326 is rotatable with respect to the upper spreader bar 324, to orient the cargo conveyance 18 for scanning. FIG. 14 is a front view of the upper portion of the scanning system 302 of FIG. 13, with the cargo conveyance 18 rotated about 90 degrees for scanning, with its long axis D1 aligned with the direction of movement B, (both out of the page in this view). The short axis E is now perpendicular to the direction of movement B. The lower spreader bar 326 and the cargo conveyance 18 may be rotated by other angles, if necessary, depending on the configuration of the radiation scanning system 300 and the crane system 302.

Figure 15:
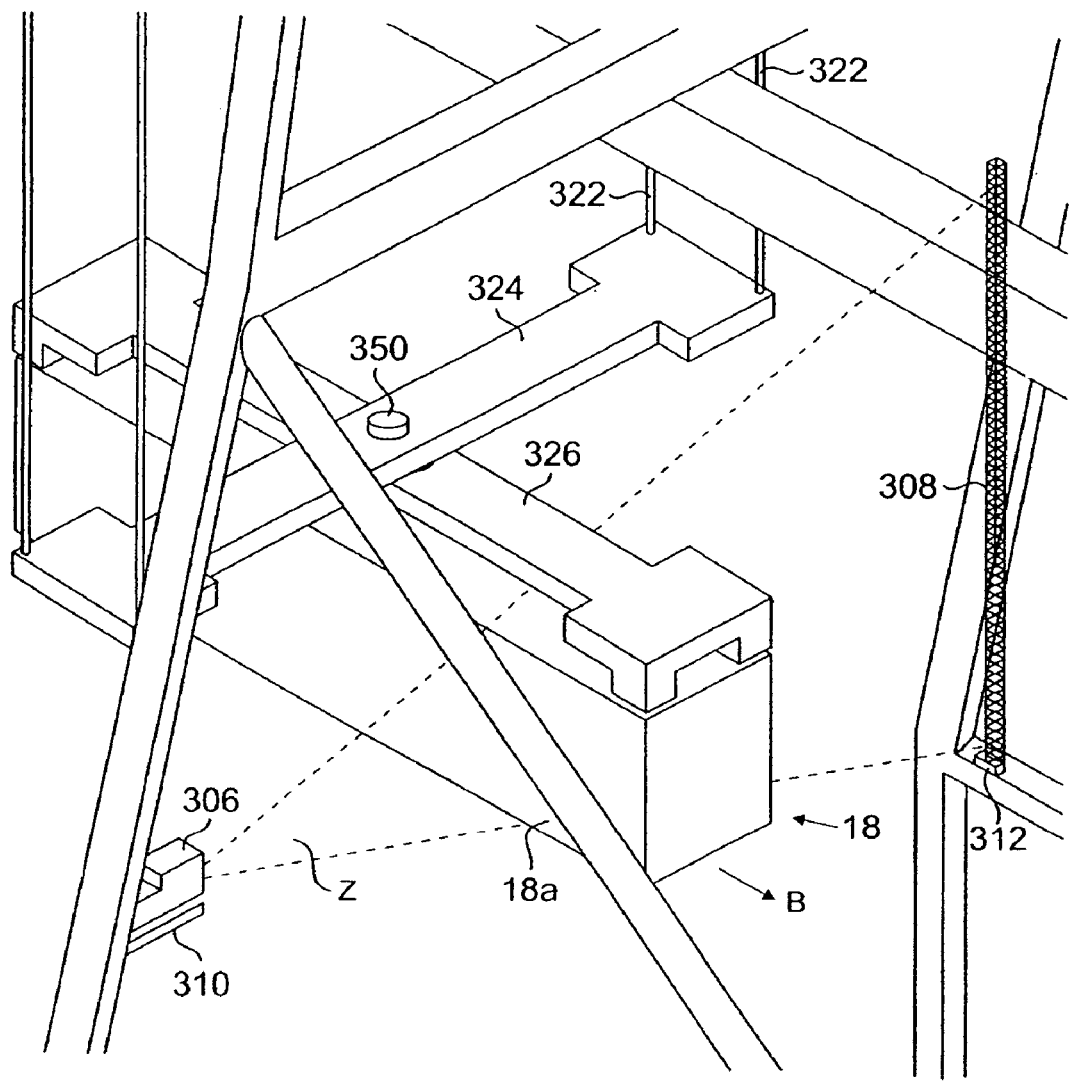
FIG. 15 is a perspective view of the cargo conveyance of FIG. 14 during scanning.

FIG. 15 is a perspective view of the cargo conveyance 18 of FIG. 14 during scanning. The cargo conveyance 18 is shown being moved along direction of movement B through a vertically diverging radiation beam Z being emitted by the source 306 and being detected by the detector 308. Additional detail of an example of the crane system 302 is also shown.

Figure 16:
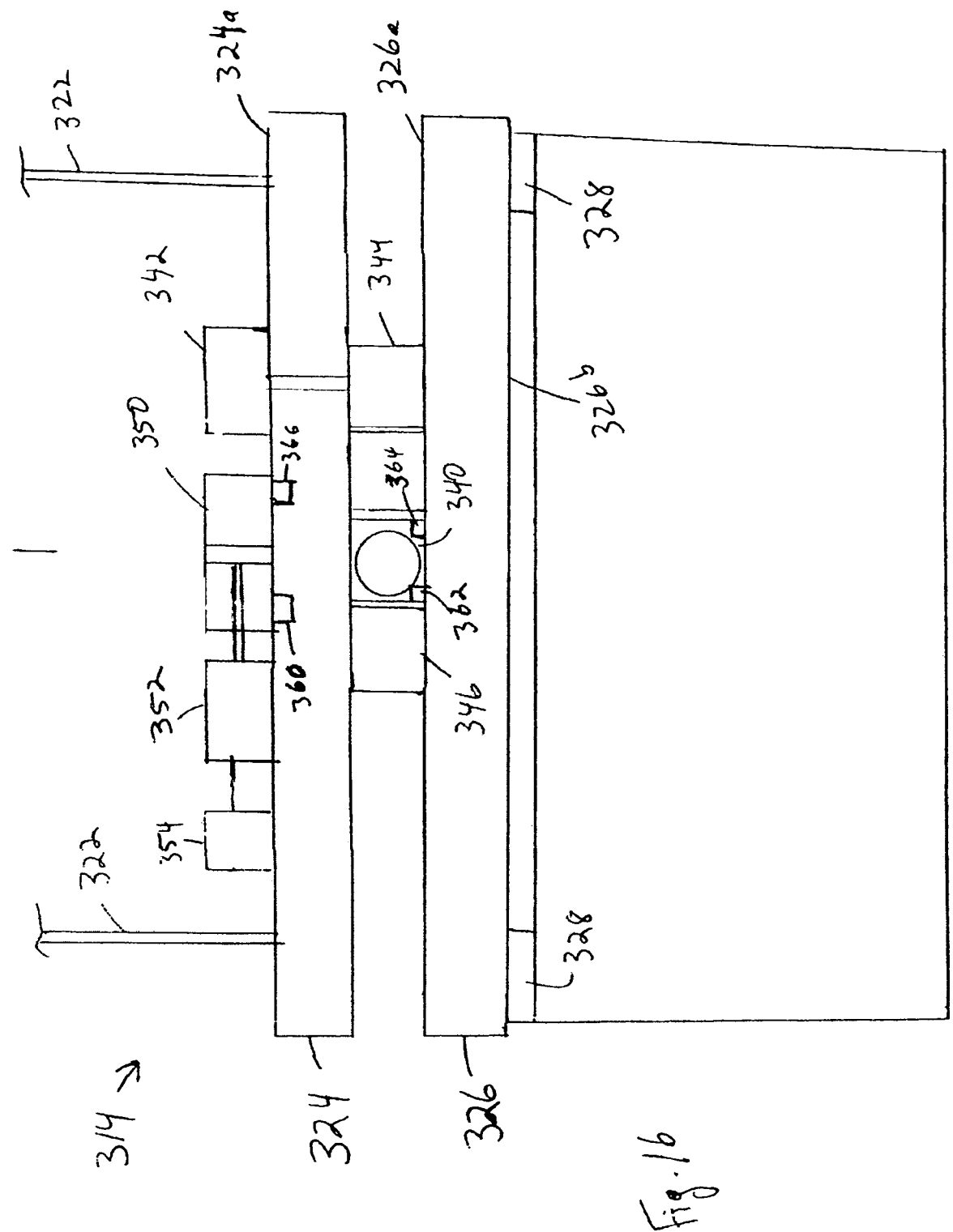
FIG. 16 is an enlarged front view of a carriage assembly supporting the cargo conveyance, in the orientation of FIG. 13, showing more detail of the assembly.

FIG. 16 is an enlarged front view of the carriage assembly 314 supporting the cargo conveyance 18, in the orientation of FIG. 13, showing more detail of the assembly. The upper spreader bar 324 and the lower spreader bar 326 are coupled to each other through a kingpin (not shown) and the bearing 340. The bearing 340 may comprise a ball bearing or other mechanism that provides a low friction connection.

A rotation motor 342 on a top surface 324a of the upper spreader 324 drives a first gear 344 between the upper spreader bar 324 and the lower spreader bar 326. A second, stationary gear 346 is attached to the upper surface 326a of the lower spreader bar 326, concentric with the bearing 340. Rotation of the motor 342 causes rotation of the first gear 344 in one direction, causing rotation of the second gear 346, the lower spreader bar 326, and the cargo conveyance 18, in an opposite direction. The rotation motor 342 may be a 10 horsepower motor, for example.

A typical cargo conveyance 18 weighs several tons. Rotation of such a mass generates a significant amount of angular momentum that would cause the upper spreader bar 324 to rotate in an opposite direction to the lower spreader bar 326, to conserve angular momentum. Such rotation of the upper spreader bar 324 would exert twisting forces on the cables 322, disrupting movement and precise positioning of the cargo conveyance for scanning, placement on the ship 21 or on a truck 35, for example. In accordance with an embodiment of the invention, a torque (force X distance) is provided to offset a change in angular momentum of the lower spreader bar 326 and cargo conveyance 18, to conserve the total angular momentum of the carriage assembly 314, thereby minimizing or preventing rotation of the upper spreader bar 324. In one example, the carriage assembly 314 is equipped with a rotatable member that is driven to rotate in a direction opposite to the direction of rotation of the lower spreader bar 326 and cargo conveyance 18, to counterbalance their angular momentum. In one example, the rotatable member is a flywheel coupled to the upper spreader 324. The flywheel may comprise a rotatable disk or wheel, for example.

In FIG. 16, a flywheel 350 is provided on top of the upper surface 324a. A flywheel drive motor 352 and a motor drive controller 354 are provided, as well. The drive controller 354 is a processing unit configured to calculate the angular momentum of the cargo container 18, as well as the angular momentum of the flywheel 350, and to control the speed of rotation of the flywheel.

The flywheel 350 is preferably of relatively low mass. The flywheel 350 may be from about 500 to about 700 pounds (from about 227 kg to about 341 kg), for example. It is also preferred that the mass be concentrated along the edge of the flywheel 350. For example, a portion of the flywheel along its edge may be a heavier material than a portion of the flywheel interior to the edge. The interior material may be steel, for example, and the material along the edge may be tungsten or lead, for example. In one example, in a flywheel 350 having a radius of 0.75 meters, the first 0.50 meters may be a steel disk and the next 0.25 meters may be a tungsten ring or a lead ring attached around the edge of the steel disk. The ring may also be thicker than the steel disk to accommodate additional mass without excessively extending the radius of the flywheel 350. When the motor 342 is activated to rotate the lower spreader bar 326 and the cargo conveyance 18, the flywheel drive motor 352 rapidly rotates the flywheel 350 in an opposite direction. The motor 342 may be a 2 horsepower motor, for example.

In one example, the flywheel 350 has a mass of 500 pounds (227 kg), a diameter of 1.5 m, and is configured as described above. The mass of the cargo conveyance 18 is 45 tons (41 metric tons). The cargo conveyance 18 is 45 feet (14 m) long. The flywheel 350 in this example may be modeled for calculation purposes as a hoop with a diameter of 1.5 m and a mass of about 250 kg, for example. The cargo conveyance may be modeled as two masses, each having half the total mass of the cargo conveyance 18, 45 feet apart, for example.

Angular momentum is equal to (Mass of Container)×(Speed of Rotation)×(Torque Arm). To counterbalance the angular momentum of the cargo conveyance 18 and the lower spreader bar 326 (which have much higher mass and a longer torque arm than the flywheel 350), the lighter flywheel 350 needs to be rotated rapidly. Thus, if the cargo conveyance 18 in this example is rotated by the motor 342 at about 0.25 RPM in one direction, the flywheel 350 would need to be rotated at about 800 RPM in the opposite direction to counter balance the angular momentum of the lower spreader arm and the cargo conveyance 18. Since the weight of the lower spreader arm 326 is very small compared to the weight of the cargo conveyance 18, its weight can be ignored.

The weight of the cargo conveyance 18 is known or may be determined based on a shipping manifest or a strain gauge sensor 364 adjacent to the bearing 340, for example. Deviations due to uncertainty in the actual weight of the cargo conveyance 18 and operation of the motors 342, 352, as well as the modeling of the flywheel 350, cargo conveyance 18, and the carriage assembly 314, could result in differences in angular momentum from that expected, that could result in twisting of the carriage assembly 314. To ensure that the flywheel 350 is rotating at a proper speed to offset the angular momentum of the cargo conveyance 18 and lower spreader arm 326, a sensor 360 is preferably provided to measure the speed of rotation of the flywheel 350. The sensor 360 may be a magnetic pick up sensor or an optical encoder, for example, which are known in the art. A sensor 362 is also preferably provided to measure the speed of rotation of the lower spreader bar 326 and the cargo conveyance 18. The sensor 362 may be a magnetic pickup sensor adjacent to the bearing 340 or an encoder on the shaft adjacent to the bearing, for example. The sensors 360, 362 provide feedback data that may be used to adjust the speed of the flywheel 350.

As mentioned above, in FIG. 16, the sensor 364 is located adjacent to the bearing 340. The sensor 364 may also be located at one or more of the cables 362 or on the kingpin (not shown). While preferred, the sensor 364 is not required. Weight information about the cargo conveyance 18 may be obtained from the shipping manifest, instead. This information may be manually entered into a computer (not shown) located in the operator compartment 320. A bar code on the cargo conveyance 18 may identify the associated manifest. In this example, the computer sends the information to the motor drive controller 354.

After calculating the actual angular momentum of the cargo conveyance 18 based on the speed and weight information, the motor drive controller 354 calculates the optimal speed of rotation of the flywheel 350 to counteract that angular momentum and compares it to the actual speed of the flywheel 350. If the optimal speed and the actual speed are different, the motor drive controller 354 regulates the speed of rotation of the flywheel 350 by means of the flywheel drive motor 352 and/or a braking system 366. The braking system may comprise a regenerative braking system, an eddy current braking system, or a friction type breaking system for example. The data from the sensor 362 may also be used by the controller 354 to determine how far the cargo conveyance 18 has been rotated and if rotation of the conveyance may be stopped. The drive controller 354 is also coupled to the motor 342 to control rotation of the cargo conveyance 18. A separate controller may be provided, as well.

The source 306 may be situated up to about 15 feet (4.6 meters) from the face 18a of the cargo conveyance 18 and may generate a radiation beam Z covering the height H of the conveyance 18 while the beam propagation angle Z spans up to, for example, 30 degrees, as shown in FIGS. 14 and 15. By passing the length L of the conveyance 18 by the radiation source 306, the contents of the conveyance 18 may be scanned. The detector 308 may be about 4.5 m to about 5 m tall.

It should be noted that the location of the source 306 and the detector 308 with respect to crane system 300, as well as the angle of the beam generated by the source 306, are examples; other configurations may be provided wherein the location of source and detector, and the angle of radiation beam generated by source, are different. In addition, the radiation source 306 and/or the detector 308 may be supported on a structure proximate the crane system 300, such as a supporting structure supported by the seaport within a profile of the crane system, as described above with respect to FIG. 8, as well as being attached to the crane system. The supporting structure or the crane system 300 may be movable along rails along the seaport, as discussed above with respect to FIGS. 9 and 10.

Figure 17:
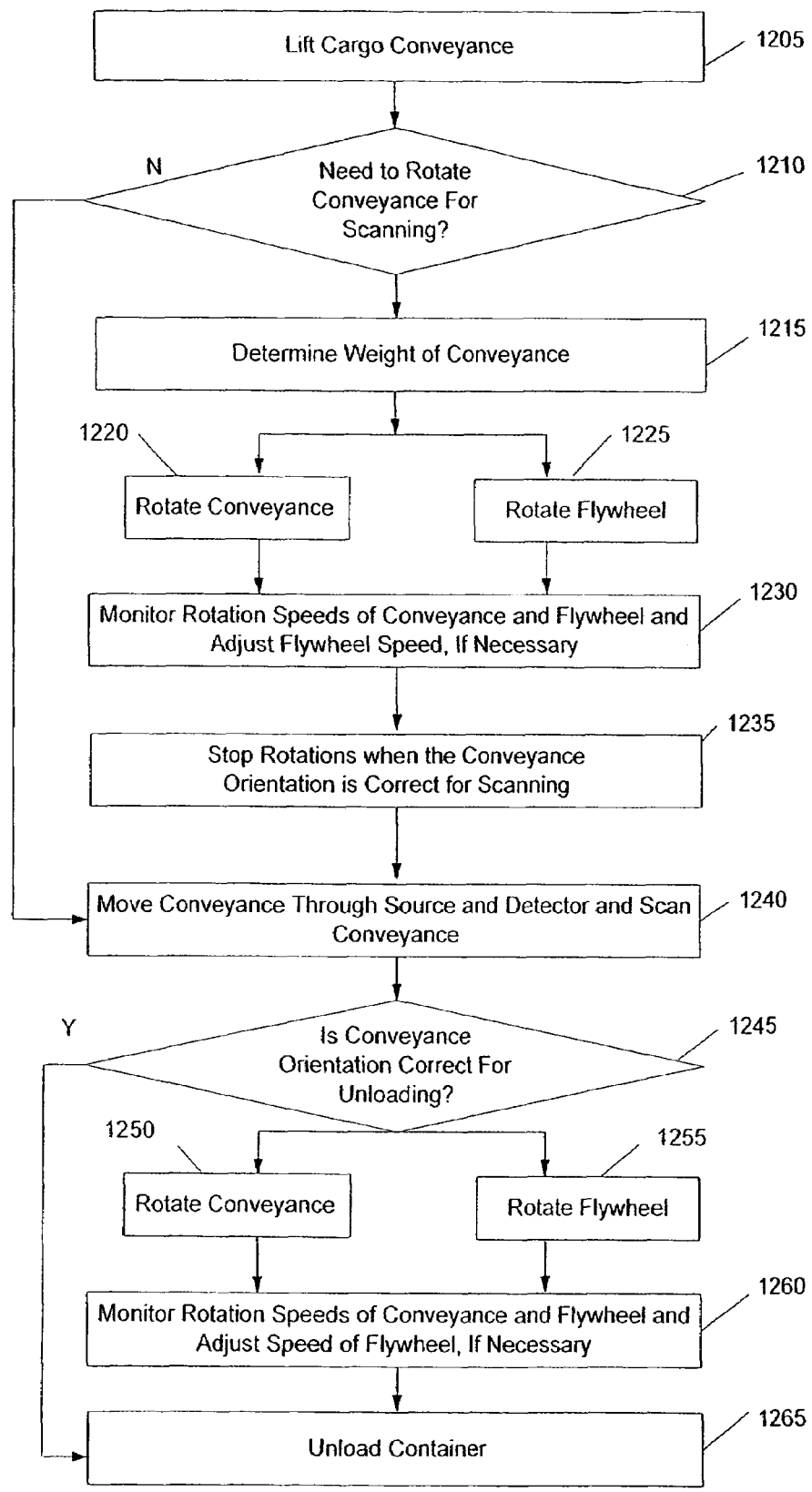
FIG. 17 is an example of a method of operating the crane scanning system of FIG. 13, in accordance with an embodiment of the invention.

FIG. 17 is an example of a method of operating the crane scanning system 300 in accordance with an embodiment of the invention. A cargo conveyance is unloaded from a ship at a dock, in Step 1205. To unload a cargo conveyance 18, the crane system 300 lowers the carriage assembly 314 to a position above a conveyance. The lower spreader bar 326 is coupled to the cargo conveyance 18 by couplers 326, or other means known in the art, and the carriage assembly is raised. The carriage assembly 314 is then moved along the direction B, along the boom 316.

In this example, a determination is made whether to rotate the cargo conveyance 18, in Step 1210. This may be determined by an operator visually or based on the shipping manifest, for example. If the cargo conveyance is properly oriented for scanning by the system, the conveyance is moved through the source and detector for scanning, in Step 1240. If the orientation of the cargo conveyance 18 is such that the conveyance is not in the proper orientation for scanning (the longitudinal axis of the conveyance is not substantially parallel to the direction of movement B of the conveyance as it is moved through the system), then the conveyance needs to be rotated for scanning. In another example, it is presumed that the cargo conveyance 18 needs to be rotated.

At a predetermined location prior to passing the source and detector, the motor drive controller 342 is instructed (by an operator located in operator compartment 320 or automatically, for example) to rotate the lower spreader bar 326 and the cargo conveyance 18, in Step 1220. In this example, the lower spreader bar 326 and the cargo conveyance 18 are rotated 90 degrees in a counterclockwise direction. The movement of the carriage assembly 314 along the direction B may be stopped during rotation, but that is not preferred.

If the cargo conveyance 18 needs to be rotated, the weight of the conveyance 18 is determined, in Step 1215. As described above, this may be determined by referring to the conveyance's shipping information (such as a shipping manifest) or by a sensor, such as the sensor 364. The weight information is sent to the motor drive controller 354 to calculate a required speed of rotation of the flywheel 350 to offset the expected angular momentum to be generated by rotation of the cargo conveyance 18, based on its weight and a predetermined rotation speed.

The lower spreader bar 326 is then rotated in a first direction at the predetermined speed, in Step 1220, to rotate the cargo conveyance 18. Rotation of the flywheel 350 in a second direction opposite to the first direction also begins simultaneously, at the speed calculated by the controller 354, in Step 1225. The speed of rotation of the cargo conveyance and of the flywheel 350 are monitored by sensors, such as the sensors 360, 362, and the speed of rotation of the flywheel is adjusted by the flywheel drive motor 353, if necessary, in Step 1230, to ensure optimum offset off the angular momentum of the rotating cargo conveyance 18.

When the cargo conveyance 18 has been rotated sufficiently to be in a proper orientation for scanning, rotation of the cargo conveyance and the flywheel are stopped, in Step 1235. The sensor 362 enables the controller 352 to determine whether the conveyance has been properly oriented for scanning, for example.

Once the cargo conveyance 18 is properly oriented, with its long axis aligned with the direction of movement B, the cargo conveyance 18 is scanned, in Step 1240, by moving the conveyance through the radiation beam.

Next, the motor driver controller 354 determines whether the cargo conveyance 18 is properly oriented for unloading, in Step 1245. For, example, if the cargo conveyance 18 is to be placed onto a truck 35 that is parallel to the axis of a ship 21, it would need to be rotated. The cargo conveyance 18 is then rotated, in Step 1250. The cargo conveyance 18 may be rotated 90 degrees, clockwise or counterclockwise. The flywheel is also rotated, in Step 1255, and the speed of rotation monitored and adjusted if necessary, in Step 1260, as described above. The cargo conveyance 18 is then unloaded, in Step 1265. In this example, the cargo conveyance 18 is placed directly onto the truck 35 and the truck can drive off. It may also be desirable to place each cargo conveyance 18 in a predetermined orientation on a dock.

A typical cargo conveyance 18 that is about 50 feet (15.2 m) long may be scanned in about 30 seconds. This is fast enough so that no or only a small delay is caused in the loading/unloading process of typical crane systems at seaports. The results of the scanning may be sufficient to evaluate whether the conveyance contains contraband and should not be shipped. Optionally, the cargo conveyance scanning may be used to screen suspect conveyances for further inspection.

The foregoing merely illustrates the principles of the invention. It will thus be appreciated that those skilled in the art will be able to devise numerous other arrangements that embody the principles of the invention and are thus within the spirit and scope of the invention, which are defined by the claims below.

What is claimed is:

1. A radiation scanning system for scanning an object, comprising:
   a crane system to move the object from a first location to a second location;
   a radiation source proximate to the crane system;

a radiation detector proximate to the crane system, the radiation detector positioned to receive radiation interacting with an object;

wherein the source and detector are positioned such that an object may be moved between the source and the detector by the crane system; and a carriage coupled to the crane system to engage the object and to move the object from the first location to the second location;

the carriage comprising:

a first member coupled to the crane system;

a second member rotatably coupled to the first member to be rotated in a first direction and capable of being coupled to the object; and a rotatable member coupled to the carriage for rotation in a second direction opposite to the first direction, to counterbalance, at least in part, angular momentum generated during rotation of the second member.

2. The radiation scanning system of claim 1, wherein: the rotatable member is a disk coupled to the first member.

3. The radiation scanning system of claim 1, further comprising:

a feedback system coupled to the rotatable member, to control, at least in part, a speed of rotation of the rotatable member.

4. The radiation scanning system of claim 3, wherein the feedback system comprises:

a first sensor to measure a speed of rotation of the rotatable member;

a second sensor to measure a speed of rotation of the second member;

a controller to determine a speed of rotation of the rotatable member to counteract, at least in part, an angular momentum generated by rotation of the object supported by the second member; and a motor coupled to the controller and to the rotatable member, to cause rotation of the rotatable member.

5. The radiation scanning system of claim 4, wherein the feedback system further comprises:

a braking system coupled to the controller and to the rotatable member, to slow rotation of the rotatable member.

6. The radiation scanning system of claim 4, further comprising:

a sensor coupled to the carriage to determine a weight of the object engaged by the second member.

7. The radiation scanning system of claim 1, further comprising:

a first gear coupled to the first member;

a second gear coupled the second member, the second gear coupled to the first gear; and a motor to rotate at least one of the first gear and the second gear;

wherein the second member is rotatable with respect to the first member when the motor rotates at least one of the first gear and the second gear.

8. A system for radiation scanning an object, comprising:

means for suspending an object;

means for rotating the suspended object to a predetermined orientation with respect to a radiation source, prior to scanning the object;

means for counterbalancing, at least in part, angular momentum generated by rotation of the object; and means for scanning the object by a radiation source.

9. The system of claim 8, further comprising:

feedback means to adjust the means for counterbalancing.

10. The radiation scanning system of claim 1, wherein the carriage is configured to rotate the object around an axis through the object.

11. The radiation scanning system of claim 1, wherein the carriage is adapted to engage a cargo container.

12. The radiation scanning system of claim 11, wherein the cargo container is at least about 6 meters long.

13. The radiation scanning system of claim 11, wherein the cargo container weighs at least one ton.

14. A method of radiation scanning an object, comprising:

lifting an object by a crane from a ship, in a first orientation;

rotating the object in a first direction to a second orientation, prior to scanning the object;

rotating a member in a second direction opposite to the first direction to counterbalance, at least in part, angular momentum generated by rotation of the object;

scanning the object by a radiation source in the second orientation; and detecting radiation after interacting with the object.

15. The method of claim 14, comprising rotating the object in the first direction around an axis through the object.

16. The method of claim 14, wherein the object is a cargo container.

17. The radiation scanning system of claim 16, wherein the cargo container is at least about 6 meters long.

18. The radiation scanning system of claim 16, wherein the cargo container weighs at least one ton.

19. The method of claim 14, comprising:

rotating the object at a first speed; and rotating the rotatable member at a second speed based, at least in part, on the weight of the object and the first speed.

20. The method of claim 14, further comprising:

moving the object between the source and the detector, during scanning.

21. The method of claim 14, further comprising:

rotating the object to the first orientation after detecting radiation; and lowering the object onto a truck while in the second orientation.

\* \* \* \* \*